United States Patent [19]

Toei et al.

[11] Patent Number: 4,625,569
[45] Date of Patent: Dec. 2, 1986

[54] LIQUID INJECTION DEVICE

[75] Inventors: Jun-ichi Toei, Yamaguchi; Nobuyuki Baba; Keiichi Housako, both of Kanagawa; Tetsuo Ikushige, Yamaguchi, all of Japan

[73] Assignee: Toyo Soda Manufacturing Co., Ltd., Shinnanyo, Japan

[21] Appl. No.: 691,948

[22] Filed: Jan. 16, 1985

[30] Foreign Application Priority Data

Jan. 17, 1984 [JP] Japan .................................. 59-5942
Dec. 6, 1984 [JP] Japan .............................. 59-258127

[51] Int. Cl.$^4$ ............................................. G01N 1/00
[52] U.S. Cl. ................................ 73/863.72; 73/864.83
[58] Field of Search ........... 73/863.71, 863.72, 863.73, 73/864.83, 864.84; 137/625.46, 625.47

[56] References Cited

U.S. PATENT DOCUMENTS 3,140,615  7/1964  Broeman ........................ 73/863.71
3,368,385  2/1968  Herucz, Jr. .................... 73/863.72
3,530,721  9/1970  Hrdina ........................... 73/863.72
3,964,513  6/1970  Molner ....................... 73/863.73 X
4,444,066  4/1984  Ogle et al. ................ 73/864.84 X

FOREIGN PATENT DOCUMENTS 5080  2/1972  Japan ............................... 73/863.72
58-87464  5/1983  Japan ............................... 73/863.71

OTHER PUBLICATIONS

Automatic Device for Injection and Multiple Column Switching in High-Performance Liquid Chromatography by K. A. Ramsteiner and K. H. Bohm, Journal of Chromatography, 260 (1983) (pp. 33-40).

Primary Examiner—Michael J. Tokar
Assistant Examiner—Tom Noland
Attorney, Agent, or Firm—Oblon, Fisher, Spivak, McClelland & Maier

[57] ABSTRACT

A liquid injection device, comprising:
 a pair of a rotor and a stator relatively rotatable in a face-contacting relationship under a liquid-tight state;
 a plurality of small openings penetrating through the rotor or stator and communicating to a plurality of liquid systems; and
 a plurality of bridging grooves or openings provided on the contacting surface of the rotor or stator to communicate two or more of the small openings so as to form a liquid flowing path. The rotor can be rotated to a predetermined angle in a normal or reverse direction with respect to the stator so as to communicate a desired number of small openings or cut off the communication between a desired number of small openings by the relative shift of the bridging grooves with respect to the small openings.

12 Claims, 113 Drawing Figures

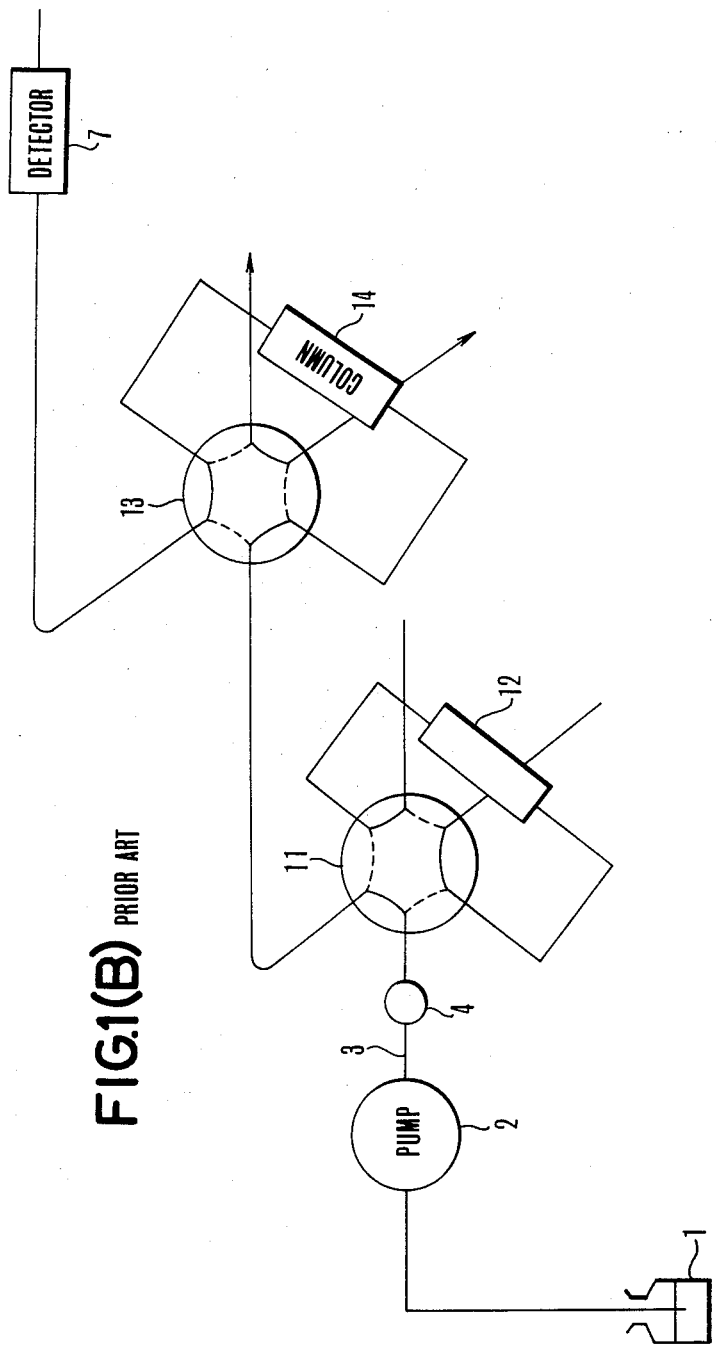

FIG.19(A)
FIG.19(B)
FIG.19(C)
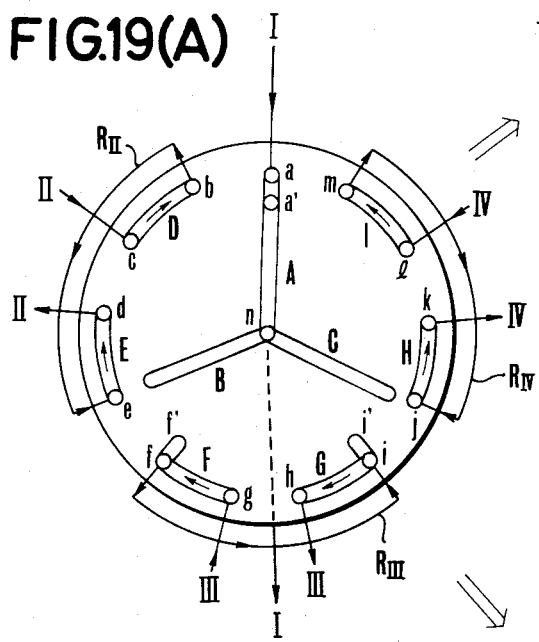
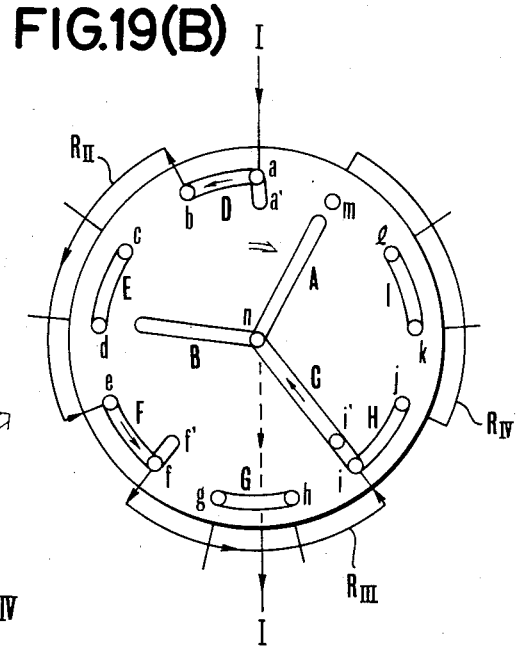
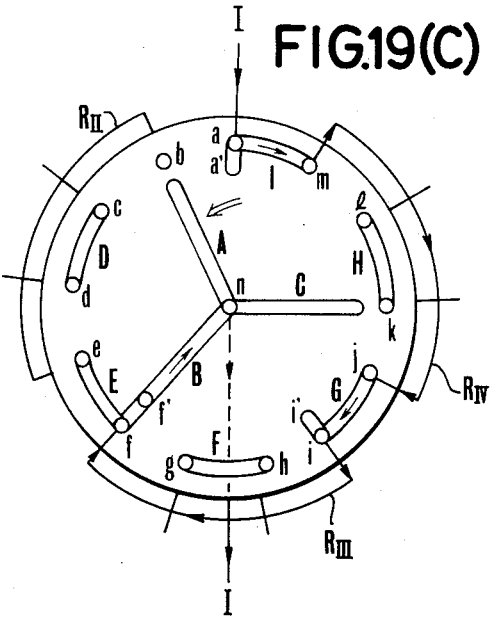

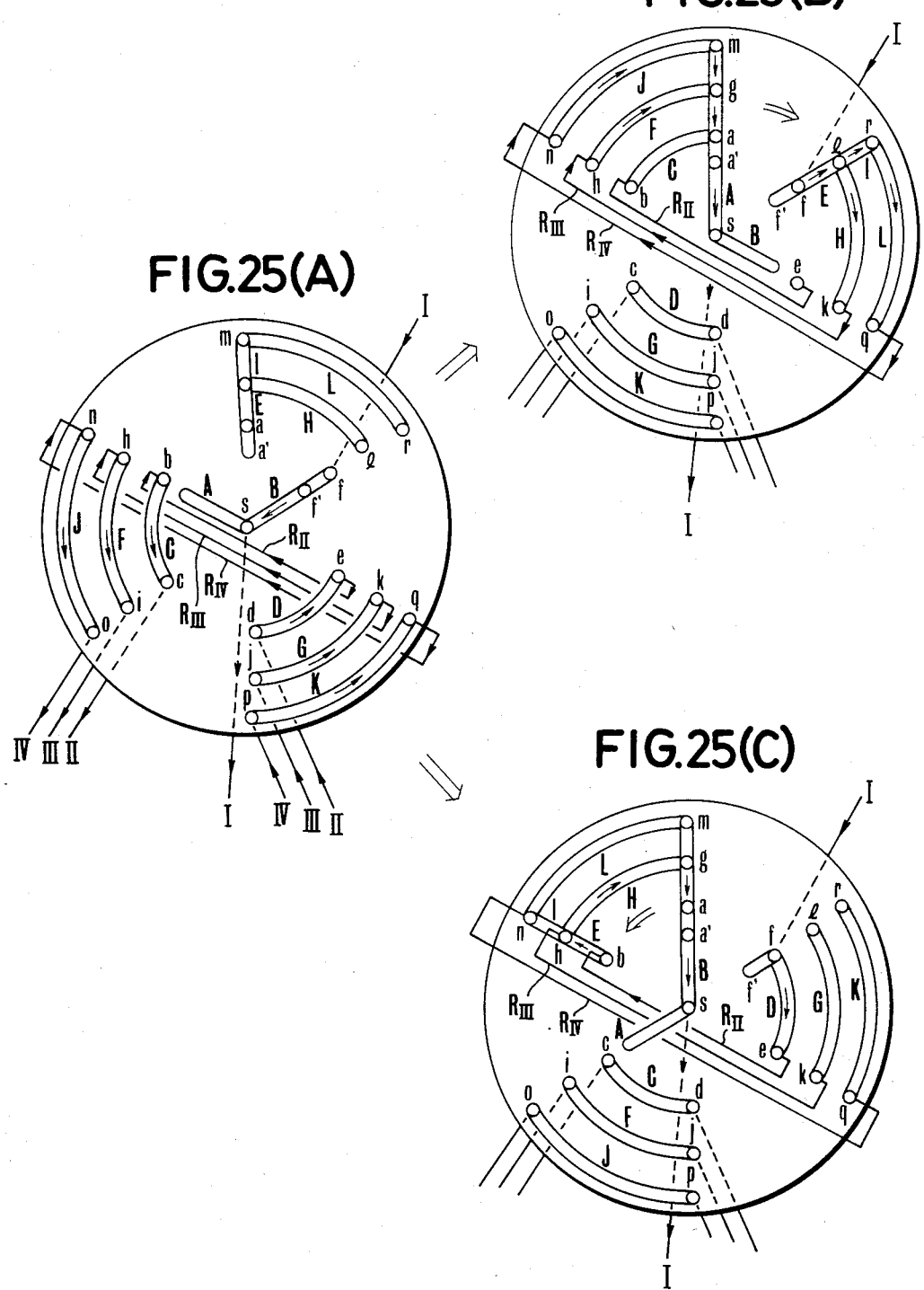

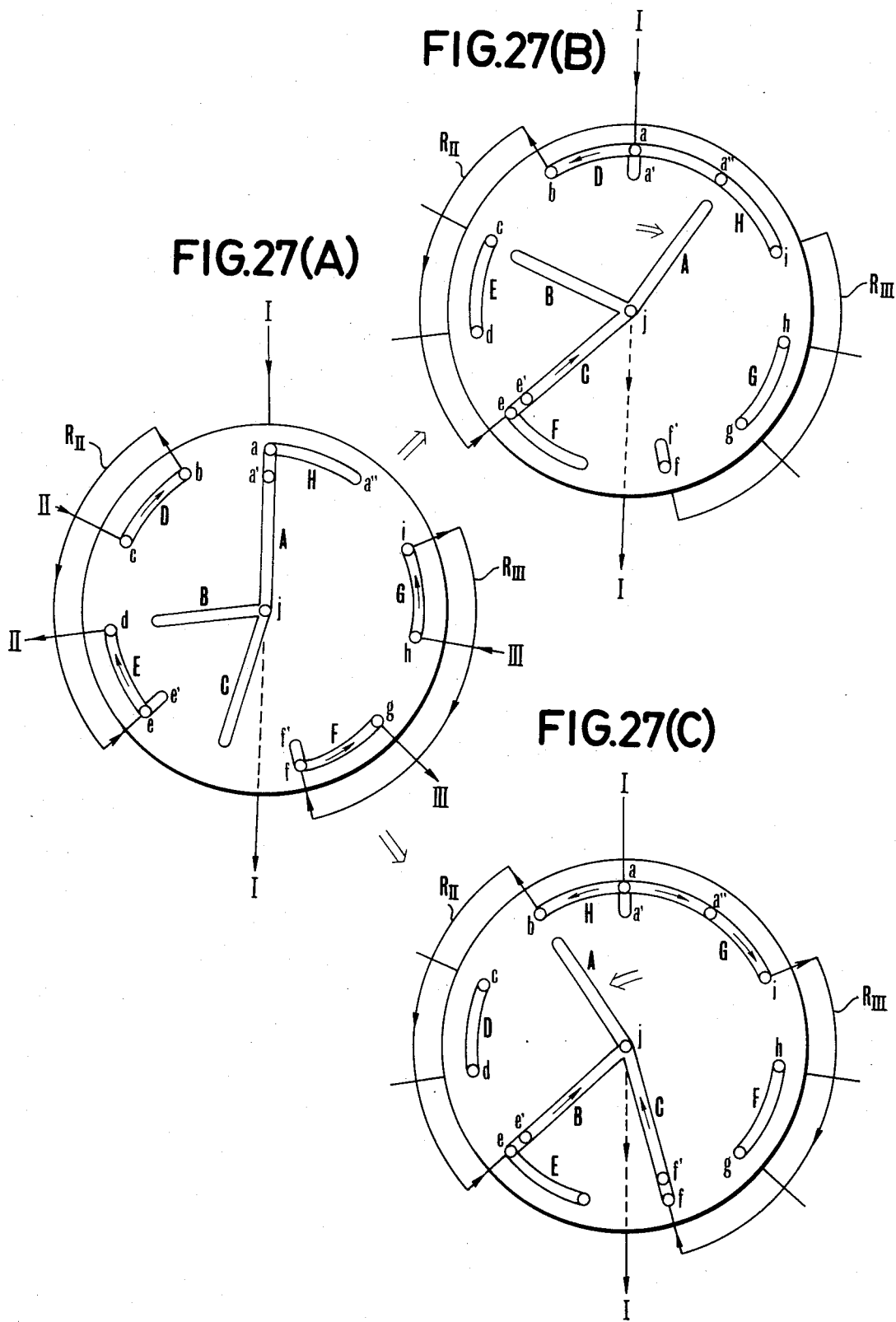

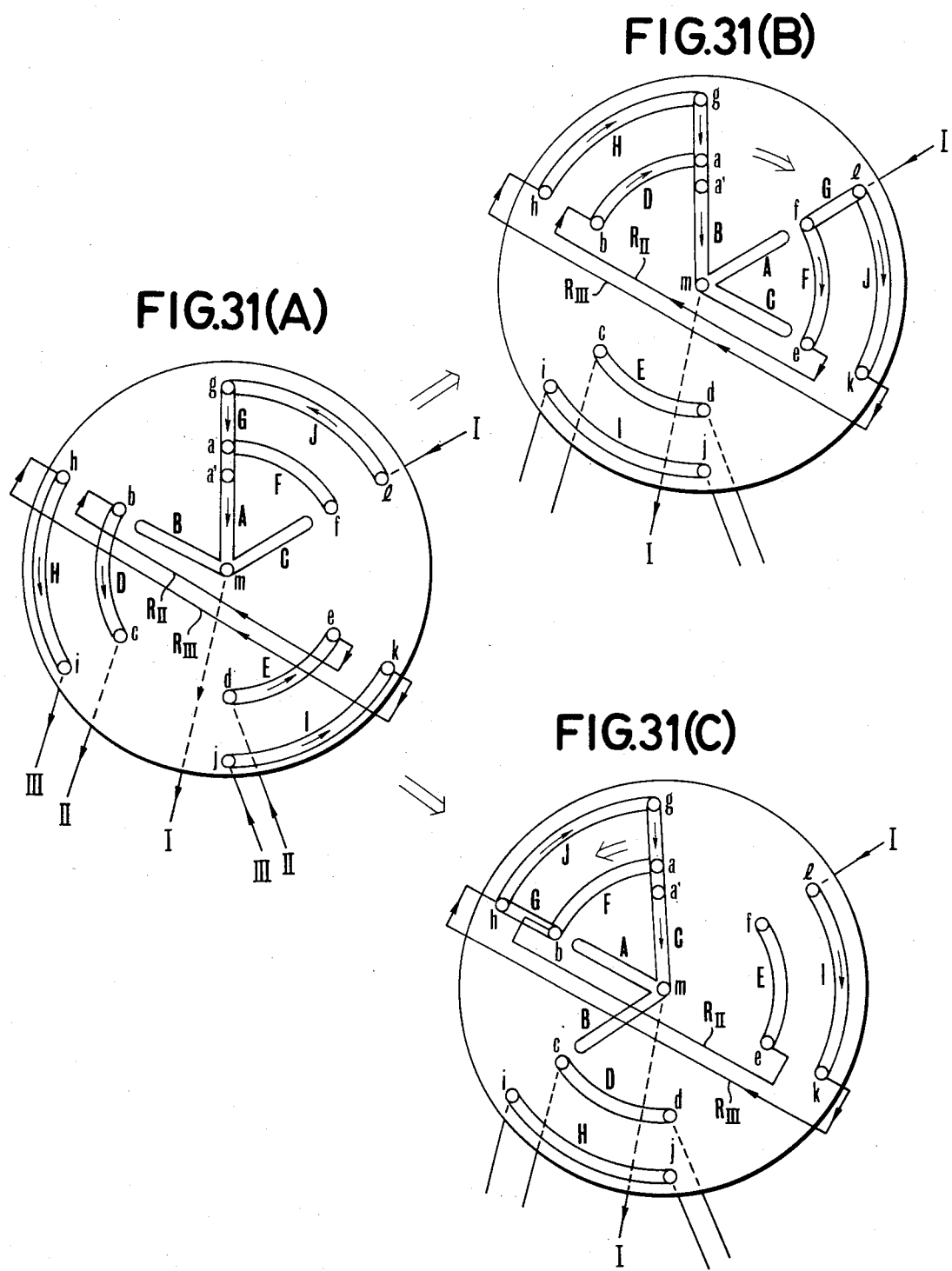

LIQUID INJECTION DEVICE

BACKGROUND OF THE INVENTION

1. Field of the Invention

The present invention relates to a liquid injection device of a multi-function type which allows for the selection of, when two or more kinds of sample solutions are injected into an eluant for example in a flow injection analysis, etc., a mode in which a plurality of sample solutions are to be injected, flow passages through which the sample solutions are fed or changeover of the flow passages.

In general, the liquid chromatography or the flow injection analysis, which are known as methods used for the analysis of certain chemical substances in a sample solution, involves injecting the sample solution into the flow of an eluant to separate or analyze the substances in a system under a rather high pressure. Therefore the injection of the sample solution is conventionally performed using a liquid injection device of a pressure-resistant type.

2. Description of the Prior Art

FIG. 1(A) is an example schematically showing a typical system of liquid injection, in a liquid chromatography wherein a known hexagonal valve 4 is used as the liquid injection device.

An outline of such a liquid injection system shall be explained. An eluant supplied to a passage 3 from an eluant tank 1 by a pump 2 normally goes through one of the paths of the hexagonal valve 4 which is in a connected relationship with the passage 3 as shown by the solid line in the drawing, is sent through a passage 5 and a resin filled column 6, and then finally to a detector 7. On the other hand a liquid supply loop 8 serving as a pipe path (which is generally made of a tube externally mounted on the valve and is simply called a loop, thus hereinafter it will be referred to as a loop) is connected to two other paths within the hexagonal valve 4, and a sample solution is sucked out of the vessel 9 by a pump 10 and thus fills the loop. The paths within the hexagonal valve 4 change over to a position as shown by the broken lines in the drawing for the purpose of injecting the sample solution as a "plug flow" into the flow of the eluant, so that the resin within the column 6 can make the prescribed separations based on the difference in affinity between the resin in the column 6 and each chemical substance in the sample solution An analysis is then made at the detector.

Here, the above-mentioned hexagonal valve 4 comprises a stator (a fixed body) and a rotor (a rotating body) arranged in surface contact with one another. The stator has a total of six small openings each at every 60° rotated position thereof. The rotor has three grooves each connecting two of six small adjacent openings, so that the connection of two adjacent openings changes each time the rotor rotates 60° as shown in the drawing. By a simple structure, a loop filling mode of the sample solution and an injection mode of a predetermined amount of the sample solution into the eluant can be secured by a rotating operation of the rotor. This valve system has been in wide use.

Also, FIG. 1(B) shows a typical system used in a case when a plurality of columns are selectively used in a liquid chromatography. An outline thereof is such that an eluant sent from an eluant tank 1 passes through the passages formed by the grooves connecting the opening as shown by the solid lines in hexagonal valves 11 and 13 and is sent to the detector 7. Therefore, in a normal condition, a sample solution injected into the eluant is separated by a column 14. However, when the passages within the hexagonal valves 11 and 13 change over as shown by the broken lines in the drawing, the specimen is separated by a column 12.

Both the flow injection analysis method and the liquid chromatography are widely used for analytical purposes. With regards to the flow injection analysis method, the reaction products resulting from the reaction of reagents with specific elements or substances in the sample solution are measured by a colorimeter or an ionic electrode, etc. This may be achieved by replacing the eluant in the liquid injection system shown in FIG. 1(A) with a reagent solution and by omitting the column 6.

As far as the liquid chromatography is concerned, the increasing requirements are such that specific chemical substances in a sample solution are analysed by utilizing the advantages resulting from the separation and the reaction as in a pre-column method or a post-column method.

Also, for the flow injection analysis method, a column is not used and only reactions between a sample solution and the reagents are used. Methods by which reactions within a flow can be advantageously performed through control of the reaction or diversification of reaction analysis are becoming very important subjects in this field.

However, in the above-mentioned liquid injection device or the passage change-over device based on a hexagonal valve or valves, the number of sample solutions which can be introduced into the liquid injection device is only one. Therefore, the injections cannot be directed into a flow of eluants having different formulations, such as sample solutions and reagents. Also in the above passage change-over device, the number of passages which can be changed over is only two, and therefore, the selection of a number of passages cannot be achieved. Thus, the conventional device of the type mentioned above lacks an important function. Also, as a method for injecting predetermined amounts of sample solutions and reagents into a flow of an eluant, for example, a method as disclosed in the Japanese Patent Laid-Open Application No. Sho 58-87464 has been proposed. The Patent Laid-Open Application discloses a method for the injection of a so-called "merging-zone type" in which a sample solution S and a reagent R are mixed together between eluants T as shown in FIG. 2(A) using two hexagonal valves, and a method for the injection of a so-called "sandwich type" in which a sample solution S is sandwiched between the reagents R as shown in FIG. 2(B). Concerning the former method for the injection of a "merging zone type": while it has an advantage that a satisfactory contact can be secured between the reagent and the sample solution, thus saving the reagent, two sets of hexagonal valves and two pumps therefor are needed. It has thus been pointed out that the device has a problem that a complete synchronization is difficult to achieve between the liquid sending state and the change-over timing of the hexagonal valves, and therefore an adverse influence over the accuracy of the analysis is unavoidable. Further, while both of the methods can simultaneously inject the sample solution and the reagent into the flow of an eluant, this function is the only one these methods can achieve, if not modified. Accordingly, they are limited in their applications.

Also, when a plurality of sample solutions of different types are to be injected into the flow of an eluant, different modes of injection for a plurality of sample solutions by the rotation of the rotor only cannot be achieved selectively. For example, it is impossible
(a) to select any one of the plurality of sample solutions for injection;
(b) to selectively carry out the simultaneous injection of a plurality of sample solutions or the injection of only a portion of said plurality of sample solutions; and
(c) to selectively change over the order of injection for a plurality of sample solutions, between a normal order and a reverse order.

Thus, they can have only a limited range of application.

OBJECTS OF THE INVENTION

One of the objects of the present invention is to provide a liquid injection device which is advantageously applicable to the cases where more than one kind of liquid such as sample solutions and reagents is to be injected into an eluant, and by which different modes of injection can be selected by a simple and precise operation, such as:
(a) selecting any one of a plurality of sample solutions and injecting the selected one;
(b) selectively carrying out the simultaneous injection of a plurality of sample solutions or the injection of only a portion of said plurality of sample solutions; and
(c) selectively changing over the order of injection for a plurality of sample solutions between a normal order and a reverse order.

Another object of the present invention is to provide a liquid injection device, by which a change-over system for injection passages and a system for changing over many kinds of injection passages can be provided by merely changing a piping channel with a desired level of precision.

SUMMARY OF THE INVENTION

The liquid injection device according to the present invention is characterized by the fact that an operation for the selective injection of two or more kinds of liquids into a constant flow of another kind of liquid may be carried out merely by rotating one rotor. The structural features of the liquid injection device reside in that the device has a pair of a stator and a rotor, which are combined so as to rotate in a mutually contacting manner under an air-tight and liquid-tight state. Either the stator or the rotor is provided with a plurality of small openings for passing supplying liquid, which respectively belong to n number (wherein n is an integer of 3 or larger) of liquid systems. A plurality of bridging grooves or slots are also provided on one of the mutually contacting and opposing surfaces of the stator and rotor so as to connect or bridge two or more of the small openings, thus forming a plurality of liquid supply paths. In this way, the rotor can be changed over in relation to the stator from its neutral position, which forms a liquid filling mode, to two other positions; that is, a normally rotated position and a reversely rotated position, which are secured by rotating the rotor a predetermined angle from the neutral position either in a normal direction or in a reverse direction, thus forming a liquid injection mode. Further, the liquid supply paths are formed so as to follow the arrangements such that:

(a) the first liquid system of the n number of liquid systems has a pair of small openings which serve as an inlet and an outlet for supplying liquid provided at one of the above-mentioned mutually contacting surfaces, the inlet and outlet being directly connected through the groove at the above-mentioned neutral position, while the direct connection is shut down at the above-mentioned normally rotated and reversely rotated positions; and (b) the (n−1) number of liquid systems, other than the first liquid system, respectively have loops spanning over an external liquid supply channel which is connected to two of the small openings and another two of the small openings, wherein each loop is connected to a respective liquid supply channel through the groove at the neutral position, and a portion of each one of the loops or the whole part thereof is connected to the inlet and the outlet of the first liquid system at the normally rotated and reversely rotated positions, in different manners depending on the direction of rotation.

In the present invention, the small openings are preferably provided in the stator, which is a fixed part. The inlet or the outlet of the first liquid system is provided at the central position of rotation of the mutually contacting surfaces of the stator and the rotor, while the other small openings are, in most cases, provided on one circle, double circles, or even multiple circles on one of the mutually contacting surfaces at predetermined angular positions.

Also the grooves respectively provided on the pair of opposing surfaces of the stator and the rotor are to be respectively connected in a bridged manner between the small adjacent openings of one circle, between the small adjacent openings in the radial direction as positioned on different circles, and further between the small opening positioned at the center of rotation of the mutually contacting opposing surfaces, as the inlet or as the outlet of the first liquid system and other small openings.

When the liquid injection device of the present invention is used, for example, for injecting very fine amounts of sample solutions and reagents, etc. into the flow of an eluant, a loop or loops are used as a liquid measuring tube, and are appropriately adjusted in their liquid filling capacity corresponding to the very fine amount to be injected (in general, a level of 20 to 100 $\mu$l).

Also, the liquid injection device of the present invention is constituted as employing column operations through the provision of a column or columns which have prescribed types of adsorbents filled therein, in a manner which intervenes in at least any one of the loops. A liquid injection device having the above described arrangement can have its liquid flow state, at times when the rotor is changed over to its normally rotated position and reversely rotated position which constitute a liquid injection mode, set in varied manners by the way in which the small openings and grooves are formed. Thus a liquid injection device with multiple functions of various types can be provided.

Now, some typical types of liquid injection device with multiple functions which may be formed according to the present invention shall be shown below.
Selective injection of more than one type of liquid:

A first liquid system forms an ordinary flow of liquid through a liquid passing path, formed by matching the positions of an inlet and an outlet, of the first liquid system at the neutral position, while the other liquid systems have their loops, acting as liquid measuring tubes, connected to the liquid filling channel so that prescribed amounts of liquid which are determined by the lengths of said loops, etc. are filled thereinto.

On the other hand, when the stator and the rotor rotate relatively to be changed over to the normally rotated position, the path between the inlet and the outlet of the first liquid system are disconnected as the bridging groove is shifted, while the connection between both ends of the loop of the second liquid system and the liquid supply and filling channel are shut off, and at the same time both of the loop ends are connected to the inlet and the outlet of the first liquid system. Also, while the connection between both ends of the loop of the third liquid system and the liquid supply and filling channel are shut off, the inlet and outlet of the third liquid system to/from the first liquid system are connected. Therefore, the liquid supply path formed between the above-mentioned pair of opposing surfaces of the stator and the rotor form a passage running as: the inlet of the first liquid system→the loop of the second liquid system→the outlet of the first liquid system. As a result, the liquid from the second liquid system can be injected into the flow of the first liquid system.

Also, when the stator and the rotor are changed over to the reversely rotated position by rotating the same, a path between the inlet and the outlet of the first liquid system is disconnected as the groove is shifted, while the connection between both ends of the loop of the second liquid system and the liquid supply and filling channel is shut off, and the inlet and outlet of the first liquid system are not connected. Also, the connection between both ends of the loop of the third liquid system and the liquid supply and filling channel is shut off, and at the same time both of the ends of the loop are connected to the inlet and outlet of the first liquid system.

Therefore, the passage formed between the pair of opposing surfaces of the stator and the rotor forms a passage such as the following:

Inlet of the first liquid system→loop of the third liquid system→outlet of the first liquid system. As a result, the liquid of the third liquid system can be injected into a flow of the first liquid system.

A liquid injection device as described above can be used in the flow injection analysis method by providing an eluant I as the first liquid and a sample solution $S_1$ and a sample solution $S_2$ as the second and third liquids, respectively.

Further, a liquid injection device of a three position change-over type applicable for the injection of three or more different kinds of liquids can be provided. This type of device is characterized in that there are a plurality of small openings at each liquid system which belong to n number of liquid systems (wherein n is an integer of 3 or larger) provided in the stator (or the rotor). One of the n number of liquid systems (the first liquid system) has small openings as an inlet and an outlet which are shut off at the normally rotated position or the reversely rotated position as the rotor rotates from the neutral position in the normal direction or in the reverse direction. Further, the (n−1) number of other liquid systems have their respective sets of small openings which are to connect both ends of their respective loops to the liquid filling channel or to the inlet and outlet in a manner so as to change them over. Also, it may be designed based on a condition such that, when the small openings are positioned on the same single circle, the number of small openings needed will be:

$$2+4\times(n-1)=4n-2$$

(wherein n is an integer 3 or larger, indicating the number of liquid systems). The circumferential positions of the small openings may be placed on radial lines divided by an angle with a value obtained by dividing 360° by $4+4\times(n-1)=4n$. Alternatively, when the small openings are located on the same circumference, they may be placed on radial lines divided by an angle with a value obtained by dividing 360° by $1+4\times(n-1)=4n-3$ when the inlet or the outlet of the first liquid system is located at the center of the stator.

Also, when the necessary number of small openings are positioned on multiple concentric circles, the device may be designed based on a condition such that a number of concentric circles as represented by m may be given by: $m=n-1$ (wherein n is an integer of 3 or larger, indicating the number of liquid systems), and the number of small openings needed will be given by:

$$2+4\times(n-1)=4n-2$$

The positions of these small openings on the circles may be placed on radial lines divided by an angle with a value obtained by dividing 360° by 6. The inlet or the outlet of the first liquid system out of the n number of liquid systems may be given at the center of the circle. Simultaneous injections of a plurality of liquids and injection of only a portion of the plurality of liquids:

The first liquid system forms an ordinary flow of liquid through a liquid passing path obtained by matching the positions of an inlet and outlet with a groove, while the other liquid systems have their loops connected to the liquid supply and filling channel. The loops are filled with a prescribed amount of liquid as determined by their length, etc.

On the other hand, when the stator and rotor are rotated relative to each other and are changed over to the normally rotated position, the path between the inlet and the outlet of the first liquid system is disconnected as the groove is shifted, while the second and third liquid systems have connections between both ends of their loops, and the liquid supply and filling channel is shut off. At the same time, both ends of the loops are connected to the inlet and outlet of the first liquid system.

Therefore, the liquid passing path formed by the pair of opposing surfaces of the stator and the rotor will go through fork-shaped branch paths having loops, respectively as in:

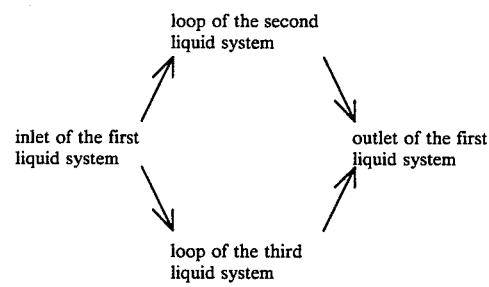

As a result, two kinds of liquids can be injected as the "merging zone type" into the flow of the first liquid system.

Also, when the stator and the rotor are rotated relative to each other and are changed over to the reversely rotated position, the path between the inlet and the outlet of the first liquid system is disconnected as the groove is shifted, while the connection between both ends of the second liquid system and the liquid supply and filling channel is shut off, and the second liquid system is connected to the inlet and the outlet of the first liquid system. Also, while the connection between both ends of the loop of the third liquid system and the liquid supply and filling channel is shut off, there will not be any connection between the inlet and outlet of the third liquid system to/from the first liquid system.

Therefore, the liquid passing path formed between the pair of opposing surfaces of the stator and the rotor will form a passage such as:

Inlet of the first liquid system→the loop of the second liquid system→outlet of the first liquid system. As a result, the liquid of the second liquid system can be injected into the flow of the first liquid system.

The liquid injection device described above can also be used as is, in a flow injection analysis method as the first liquid system is used for an eluant I, and the second and third liquid systems are used for sample solution $S_1$, and sample solution $S_2$.

Further, such a type of liquid injection device can be used for injection of three or more kinds of liquid. Therefore, a liquid injection device of a three position change-over type can be characterized by such a feature that there are a plurality of small openings in each system belonging to n number (wherein n is an integer of 3 or larger) of liquid systems, provided in the stator (or the rotor), and one of the n number of liquid systems (the first liquid system) has small openings serving as an inlet and an outlet which are connected to each other at the neutral position but are shut off from each other at the normally or reversely rotated position secured by a rotation of the rotor from the neutral position to the normal or reverse direction. The (n−1) number of other liquid systems have their respective sets of small openings which connect both ends of their respective loops to the liquid filling system and to the other liquid systems. The liquid injection device can be designed based on the condition that, when the small openings are located on one circle, the number of small openings needed may be given by:

$$2+4\times(n-1)=4n-2$$

(wherein n is an integer of 3 or larger, indicating the number of liquid systems), and circumferential positions of these small openings may be placed on the radial lines divided by an angle with a value obtained by dividing 360° by $$6+4\times(n-1),$$

when the small openings are located on the same circle, and they may be placed on the radial lines divided by an angle with a value obtained by dividing 360° by $$3+4\times(n-1)=4n-1$$

when the inlet (or the outlet) of the first liquid system is located at the center of the stator.

Also, when the necessary number of small openings are positioned on multiple concentric circles, the device can be designed based on such a condition that a number of the concentric circles as represented by m may be given by $$m=n-1$$

(wherein n is an integer of 3 or larger, indicating the number of liquid systems), and the number of necessary small openings may be given by:

$$2+4\times(n-1)=4n-2$$

and further, that the circumferential positions of these small openings are placed on radial lines divided by an angle with a value obtained by dividing 360° by at least 6, and the inlet or the outlet of the first liquid system out of n number of liquid systems may be positioned at the center of the circles.

Change of the order of injection of a plurality of liquids to either before or after:

The inlet and the outlet of the first liquid system forms an ordinary flow of liquid at the neutral position through the liquid passing path formed by matching the position of a groove, while the other liquid systems have their loops connected to the liquid supply and filling channel, so that a prescribed amount of liquid as determined by the lengths of loops, etc., will be filled into the loops.

On the other hand, when the stator and the rotor are rotated relative to each other and are changed over to the normally rotated position, the path between the inlet and the outlet of the first liquid system is disconnected as the groove is shifted, while a connection between both of the loop ends of the second liquid system and the liquid supply and filling channel are shut off. At the same time, both of the loop ends are connected to the inlet of the first liquid system and the third liquid system. Also, the connection between both ends of the loop of the third liquid system and the liquid supply and filling channel is shut off, and, at the same time, both of the loop ends are connected to the outlet of the first liquid system and the second liquid system.

Therefore, the liquid passihg path formed between the above-mentioned pair of the stator and the rotor will form such a passage as:

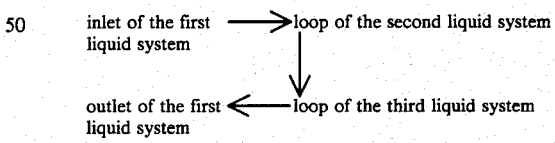

As a result, the second and third liquid systems may be injected in a series into a flow of the first liquid system.

Also, when the stator and the rotor are rotated relative to each other and are changed over to the reversely rotated position, the path between the inlet and the outlet of the first liquid system is disconnected as the groove is shifted, while a connection between both of the loop ends of the second liquid system and the liquid supply and filling channel is shut off. At the same time, both of the loop ends are connected to the outlet of the first liquid system and the third liquid system, and further the connection between both of the loop ends of the third liquid system and the liquid supply and filling channel is shut off. At the same time both of the loop ends are connected to the inlet of the first liquid system and the second liquid system.

Therefore, the liquid passing path formed between the above-mentioned pair of opposing surfaces of the stator and the rotor will form such a passage as:

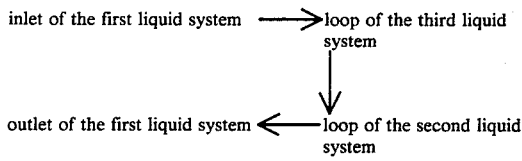

As a result, the third liquid and the second liquid are injected in a series into a flow of the first liquid, in an order reverse to that as when in the normally rotated position.

The liquid injection system as described above can also be used in a flow injection analysis method as is, by using the first liquid system for an eluant I, and the second liquid system for a sample solution S, while the third liquid system is used for a reagent R.

Further, such a type of liquid injection device can be used for the injection of three or more different kinds of liquids. Therefore, a liquid injection device of a three position change-over type can be characterized by a feature such that there are a plurality of small openings belonging to one of n number (wherein n is an integer of 3 or larger) of liquid systems, provided in the stator (or the rotor), and one of the n number of systems (the first liquid system) has small openings serving as an inlet and an outlet which are connected together at the neutral position but are shut off from each other at the normally or reversely rotated positions as being secured by rotating the rotor from the neutral position in the normal or reverse direction. Further, the (n−1) number of other liquid systems have their respective set of small openings which connect both ends of their respective loops to the liquid supply and filling channel and to the other liquid systems. Also, this liquid injection device can be designed based on the conditions such that, when the small openings are positioned on one circle, the number of necessary small openings may be given by:

$$2+4\times(n-1)=4n-2$$

(wherein n is an integer of 3 or larger, indicating the number of liquid systems), and the circumferential positions of these small openings are placed on radial lines divided by an angle with a value obtained by dividing 360° by $$2+4\times(n-1),$$

when the small openings are located on the same circle, and they are placed on radial lines divided by an angle with a value obtained by dividing 360° by $$1+4\times(n-1)=4n-3$$

when the inlet (or the outlet) of the first liquid system is located at the center of the stator.

Also, when the necessary small openings are positioned on multiple concentric circles, the liquid injection device may be designed based on a condition such that a number of the concentric circles as represented by m may be given by $$m=n-1$$

(wherein n is an integer of 3 or larger, indicating a number of liquid systems), and a number of necessary small openings may be given by $$2+4\times(n-1)=4n-2$$

and further that the circumferential positions of these small openings are placed on radial lines divided by an angle with a value obtained by dividing 360° by at least 6, and the inlet or the outlet of the first liquid system out of the n number of the liquid systems is positioned at the center of the circles.

BRIEF DESCRIPTION OF THE DRAWINGS

FIG. 14(A) is a front elevation of a rotor.

DESCRIPTION OF THE PREFERRED EMBODIMENTS

Now, explanations shall be made about the present invention based on examples shown in the attached drawings. Examples shown in FIG. 3 through FIG. 12 disclose liquid injection devices of a multi-function type used for the analysis of a sample solution, comprising small openings on the circumference of a stator for passing liquid therethrough, a selection of which can be made by merely rotating the rotor either in the normal or reverse direction for the purpose of injecting simultaneously a sample solution (second liquid) and a reagent (third liquid) into the flow of an eluant (first liquid), and also a mode to inject a sample solution only thereinto, wherein if a positional change-over to a reversely rotated position as a result of a reverse rotation of the rotor is made impossible as desired, the device can serve as a liquid injection device solely used in the mode by which two kinds of liquids are injected simultaneously. There are cases in which such an arrangement of the device is useful in eliminating the possibility of erroneous operations, for example, as in the application for the flow injection analysis.

EXAMPLE 1

Figure 1A:
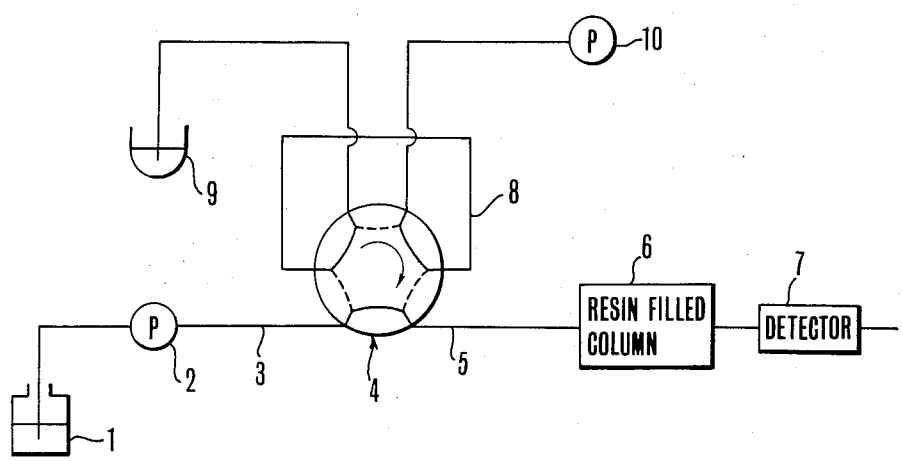
FIGS. 1(A), (B) show an example of a liquid injection device using a conventional hexagonal valve.
Figure 2A:
FIGS. 2(A), (B) show respectively the modes of injection of two kinds of liquids.
Figure 2B:
Figure 3:
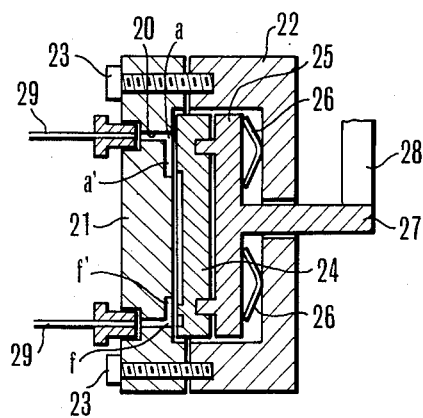
FIG. 3 is a general view of a liquid injection device in Examples 1 to 4 of the present invention.

FIG. 3 shows an outline of the arrangement for a liquid injection device in this example by way of a cross-sectional view, in which 21 is a stator of a circular plate shape, 22 is a rotor case having a circular flange 20, and the fore end of the circular flange 20 of the rotor case 22 has V-shaped cross-section that is made to engage, with the peripheral portion of the stator 21. The stator 21 and the rotor case 22 are bound firmly together by bolts 23.

A rotor 24 has an internal surface that is in a mutually contacting relationship with the internal surface of the stator 21 in an air-tight and liquid-tight state under a prescribed pressure. The driving disc 25 for rotating the rotor 24, as well as springs 26 exerting a pressing force biasing the rotor 24 against the stator 21, are housed in a hollow portion encased by the stator 21 and the rotor case 22. A rotation driving shaft 27 extends out from the rear surface of the driving disc 25 and through to the outside of the rotor case 22. What is shown as 28 is an operating handle which protrudes from the extended end of the rotation driving shaft 27 in the radial direction.

Figure 4A:
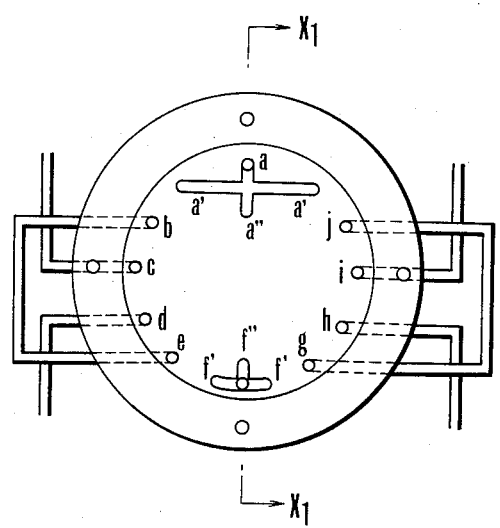
FIG. 4(A) shows a front elevation of a stator.
Figure 4B:
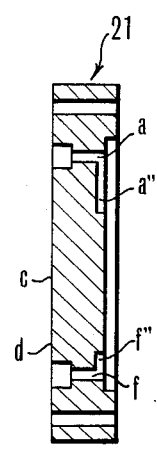
FIG. 4(B) shows a cross-sectional view taken along $X_1$-$X_1$ in FIG. 4(A).

A plurality of small openings, a to j, are formed as shown in FIGS. 4(A) and (B) at the hollow internal surface of the stator 21, the small openings a to j being connected to various external tubes 29 through connecting holes which penetrate the stator 21 through its thickness. Also, the small openings a to j are arranged such that a and f are positioned on one diametrical line of the stator and four each of the small openings, b to e, and g to j, are positioned in a symmetrical relationship, as shown in the drawing, across the diametrical line on which the small openings, a and f, are located. That is, b to e are positioned on one side of the diametrical line, and g to j, on the other side. Further, bridging grooves, a' and a", having a cross shape are provided in an associated relationship with the small opening, a, such that, while being located in a perpendicular position to each other, they also extend in the radial direction from the opening a. Bridging grooves, f' and f", which extend somewhat in the radial direction from the small opening f, to both sides in the circumferential direction are also provided in an associated relationship with the small opening f.

Figure 5A:
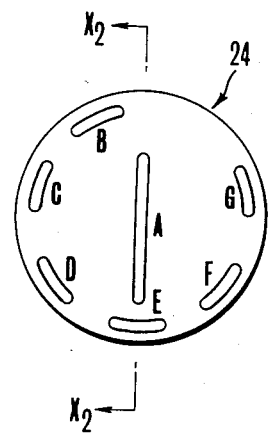
FIG. 5(A) shows a front elevation of a rotor.
Figure 5B:
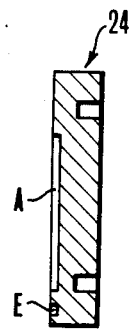
FIG. 5(B) is a cross sectional view taken along $X_2$-$X_2$ in FIG. 5(A).

Also, at the surface of the rotor 24 opposing the stator 21, as shown in FIGS. 5(A) and (B), a plurality of bridging grooves B to G, which selectively connect parts separated from each other in the circumferential direction of small openings adjacent to each other at the stator side, at relative positions in the radial direction to which the small openings a to j face, and a bridging groove A which connects the grooves a" and f" respectively connected to the small openings a and f and is formed in the diametrical direction are provided. In this example, these grooves A, and B to G are formed by providing recesses on the surface of the rotor. However, they may be formed in such a way that only the ends of the groove are opened at the surface of the rotor while the central portion between the two ends is perforated at the inside of the rotor. Also, for the benefit of the explanation, the grooves are shown in the drawing as having an increased size. However, the actual groove size and shape can be of a very fine line.

Figure 6A:
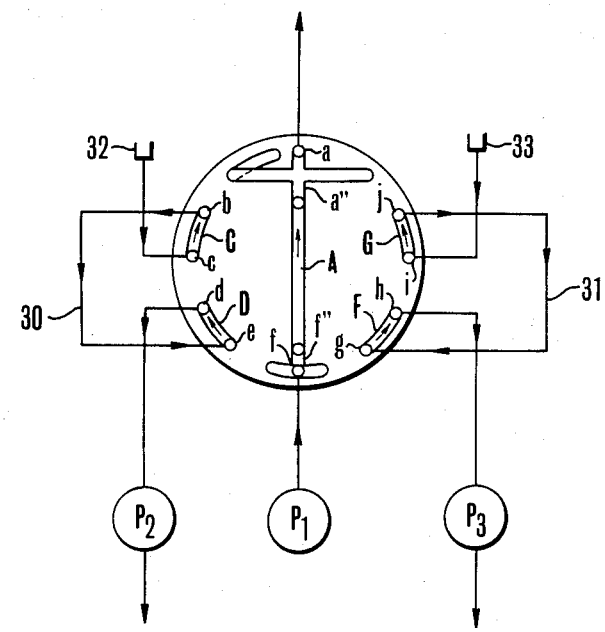
FIGS. 6(A) through (E) show states of the positional change-over of the stator and the rotor in Example 1 as shown in FIG. 3 and formation of the liquid passing paths accompanying thereto.
Figure 6B:
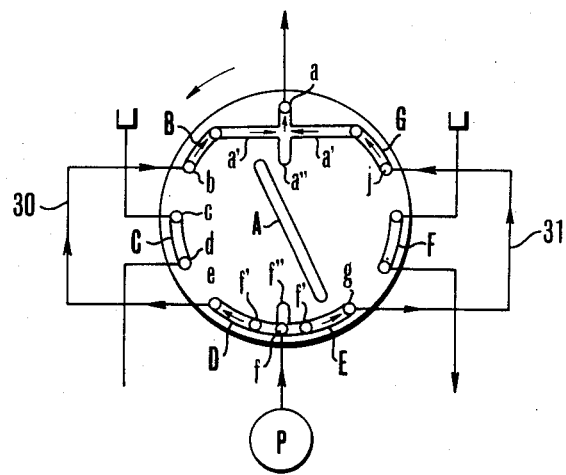
Figure 6C:
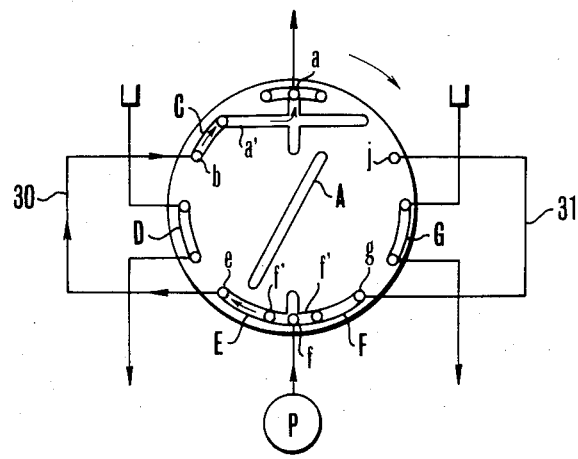

The stator 21 and the rotor 24 having the above-mentioned arrangements are in contact with each other in an air-tight state and have a relationship such that the small openings a to j and the grooves a', a", f' and f" at the stator side face the bridging grooves A to G at the rotor side as shown in FIG. 3, thus forming a liquid injection device. Then as the rotor 24 is rotated on the stator 21, it can be changed over so as to have the positional relationships as shown in FIGS. 6(A) to (C). FIGS. 6(A) to (C) schematically show the ways in which the liquid passing paths for an eluant T, a sample solution S, and a reagent R, are formed.

The above-mentioned small openings a to j are arranged such that their respective relationship with the external accessory equipment will be as shown below. That is, the opening a is an outlet for the eluant which is arranged so as to be selectively connected to any one of the paths for a flow injection and an analysis in a liquid chromatography. The opening f is an inlet for the eluant and is connected to an eluant tank (not shown in the drawing) through a pump $P_1$. The openings b and e are connected to both ends of a specimen loop 30. Also, the openings j and g at symmetrical positions in relation to the openings b and e respectively, are connected to both ends of a specimen loop 31. The openings c and d form two points within a specimen filling circuit, the opening c being connected to a specimen vessel 32, and the opening d being connected to a suction pump $P_2$. Similarly, the openings i and h, located symmetrically thereto, are arranged such that the opening i is connected to a specimen vessel 33 and the opening h is connected to a suction pump $P_3$.

FIG. 6(A) shows a state in which the stator 21 and the rotor 24 are positioned at the neutral position which corresponds to a liquid filling mode, and constitutes a basic position of this liquid injection device. Under this state, the bridging groove A on the rotor has its position matched with the grooves a", f' on the stator, the small openings a and f form a liquid passing path of f~f"→A→a"~a, and the eluant has an ordinary or normal flow from the pump $P_1$.

Also, the small openings b, c, d and e which belong to a sample solution system form a liquid passing path of c→C→b→loop 30→e→D→d by the bridging grooves C, D. The specimen loop 30 is filled with the sample solution S from the specimen vessel 32.

Similarly, the specimen loop 31 is filled with the reagent by a liquid passing path, i→G→j→loop 31→g→F→h for a reagent system.

FIG. 6(B) shows a state in which the rotor 24 is rotated slidingly against the stator 21 in the counterclockwise direction (hereinafter the counterclockwise rotation in the drawing will be called a reverse rotation, while the clockwise rotation will be called a normal rotation). As a result, the device has been changed over to a reversely rotated position, and, as a result of the rotation, the liquid passing path will change as shown below. That is, the connection (or positional matching relationship) between the bridging A and the grooves a'', f'' on the stator is released. Thus, the direct connection with the eluant T is shut off.

Also, as the bridging grooves B, C and D rotate, the connecting relationship among the small openings b to e for the sample solution system are changed as will be explained below. That is, the groove B connects the groove a' with the small opening b in the stator, and the groove C connects the small openings c and d, while the groove D connects the small opening e with the groove f' at the stator side. Therefore, the liquid passing path is formed in an order of f~f'→D→e→loop 30→b→B→a'~a between the inlet and the outlet for the eluant T, so that the sample solution S is injected into the flow of the eluant T.

The positional matching relationship between the small openings g to j for the other sample solution system and the bridging grooves E, F and G at the rotor side is also changed, and the liquid passing path therefore is formed in an order of f~f'→E→g→loop 31→j→G→a'~a between the inlet and the outlet for the eluant, so that the reagent R is injected into the flow of the eluant T.

By such an arrangement in the injection mode as secured at the reversely rotated position, the path of the eluant is divided into two branches at the inlet f. One of the branches goes through the loop 30, while the other one goes through the loop 31, and then they merge at the outlet f. Changes of these liquid passing paths are done in the state of a perfect cycle, and the merging thereof is made by flows of one eluant. Therefore the simultaneous injection of two kinds of liquid in the "merging zone type" with a high level of accuracy can be achieved.

Figure 6D:
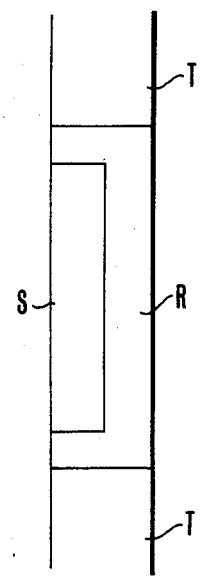

Further, when the filled amounts in the left and right loops 30 and 31 in the injection mode of this example are set so that the amount in the latter (that is, the reagent R side) is somewhat larger than the other, such an injection mode as shown in FIG. 6(D), that is, the injection of the sample solution S being encased by the reagent R can be made, so that the effect of the reaction between the sample solution and the reagent can be obtained satisfactorily as a whole.

FIG. 6(C) shows a state in which the rotor 24 is rotated on the stator 21 in the clockwise direction (normal rotation), thus changing the same over to the normally rotated position. The liquid passing path is changed by the rotation in a manner similar to that in the case of FIG. 6(B). That is, the direct connection of the eluant through the bridging groove A is shut off, and a liquid passing path for the sample solution system is formed in an order of f~f'→E→e→loop 30→b→C→a'~a, thus connecting the inlet f with the outlet a of the eluant system.

However, the reagent system is placed in a state such that the small opening j at one end of the specimen loop 31 is not bridged to any others, and the liquid passing path in this system is closed at j in the order of f18 f'→F→g→loop 31→j, thus a flow of liquid will not occur. This is derived from the fact that a bridging groove is not provided between the bridging grooves A and G in the rotor as shown in FIG. 5(A).

Figure 6E:
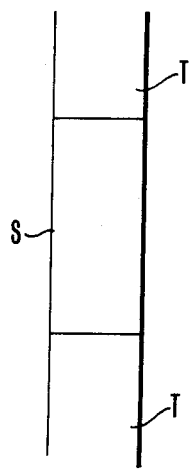

By the above arrangement, only the sample solution S in the specimen loop 30 is injected into the eluant T under the injection mode at the normally rotated position. Thus an injection of the sample solution S into the eluant T is achieved as a "plug flow" as shown in FIG. 6(E).

Also, in connection with the above explanations, the length of the bridging grooves B to G, the positioning of the small openings a to j, the lengths of the grooves at the stator side (especially of the grooves a', f'), and the angle of rotation in a change-over from the neutral position to either the normally rotated position or the reversely rotated position of the rotor are naturally set so as to correspond to the operations as described above.

According to Example 1, as explained above, either the sample solution S, alone, can be injected into the eluant T or the sample solution S and the reagent R can be simultaneously injected in the "merging zone type" by selectively rotating the rotor in the normal or reverse direction from the neutral position (which constitutes a liquid filling mode) by a mere change-over operation of the matching relationship between the stator and the rotor to the normally rotated position or the reversely rotated position. Even though the operation thereof is very simple, an excellent function is provided such that injections of two different modes can be selected. Also, the structure of the device itself consists only of a single valve mechanism. Thus, the device has great advantages in practical application.

As described already, only the positional change over from FIG. 6(A) to FIG. 6(B) for the liquid in device shown in FIGS. 3 through 6 can be made. If a positional change-over to FIG. 6(C) is made impossible by some suitable blocking means, this device will constitute a device solely used to make simultaneous injections of two kinds of liquid in the "merging zone type". Even if another bridge exists between the bridging grooves A and G of the rotor shown in FIG. 5(A), no difficulties will occur. Thus a rotor having symmetrically bridging grooves can be used.

Also, the grooves formed respectively on the stator and the rotor as mentioned above are actually of a very fine line shape. Further, the rotor, which is ordinarily made of polyimide, teflon, etc., is pressed in a mutually contacting manner against the stator under a pressing force which is large enough to secure a sufficient airtightness or liquid-tightness. Therefore, as far as the grooves are concerned, geometrically varied shapes of grooves can easily be made as long as there is no trouble in the liquid flow, so that the above-mentioned device, which can be used in a mode for the simultaneous injection of two kinds of liquids or a device of a multi-function type which can be used in a mode for the injection of only one kind of liquid together with the former mode, can have various groove shapes and various positional arrangements for the small openings.

EXAMPLE 2

Figure 7A:
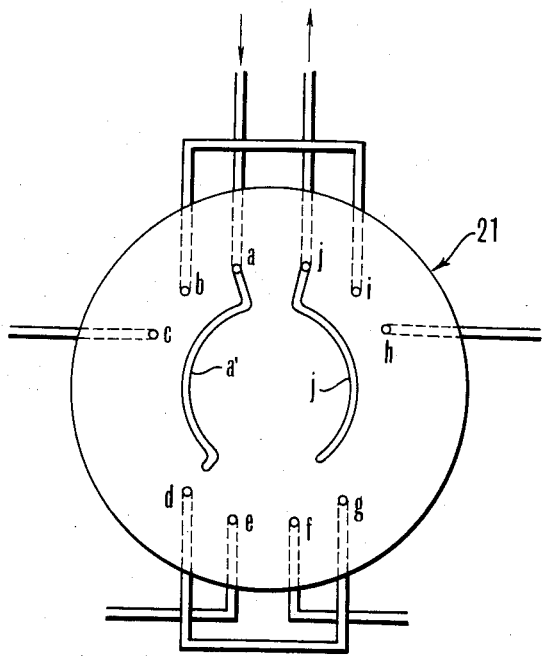
FIGS. 7(A), (B) are front elevations to show the stator and the rotor in Example 2 of the present invention.
Figure 7B:
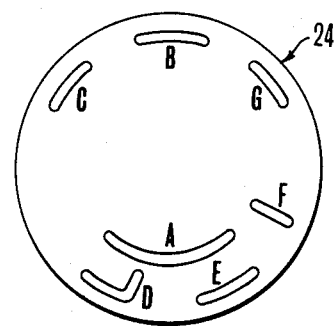
Figure 8A:
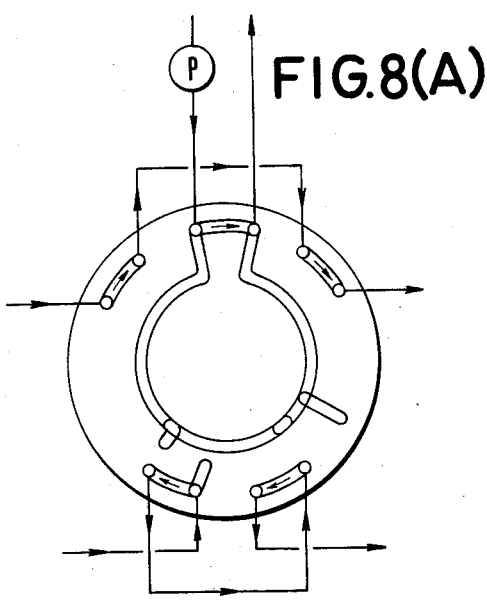
FIGS. 8(A) through (C) show states of forming liquid passing paths accompanying the positional change-over of the stator and rotor as shown in FIG. 7.
Figure 8B:
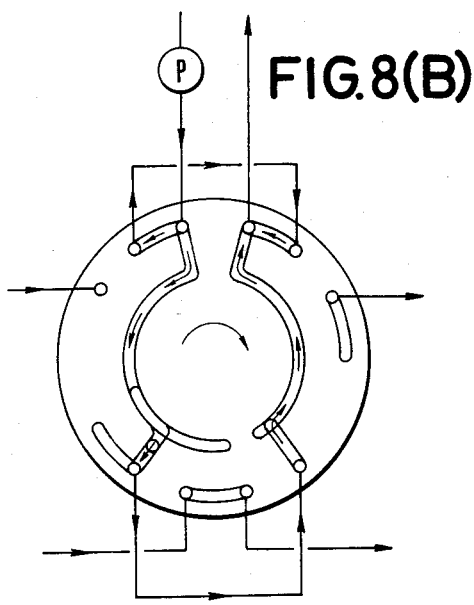
Figure 8C:
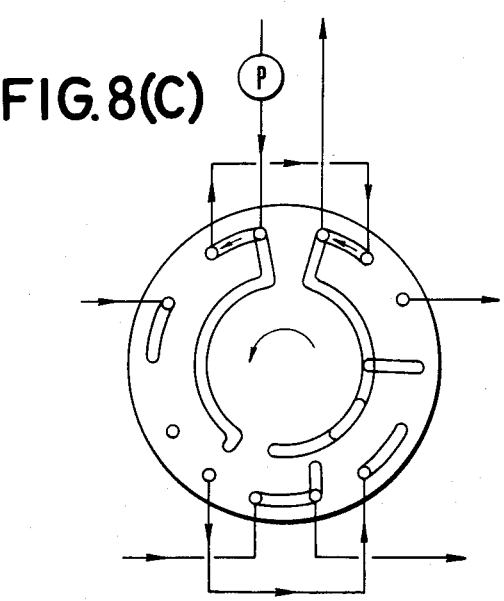

FIGS. 7(A) and (B) show a stator (A) and a rotor (B) as a modified example. FIGS. 8(A)-(C) show a filling mode at the neutral position (A), a simultaneous injection mode for two liquid types at the normally rotated position (B), and an injection mode for one liquid type at the reversely rotated position (C), respectively.

EXAMPLE 3

Figure 9A:
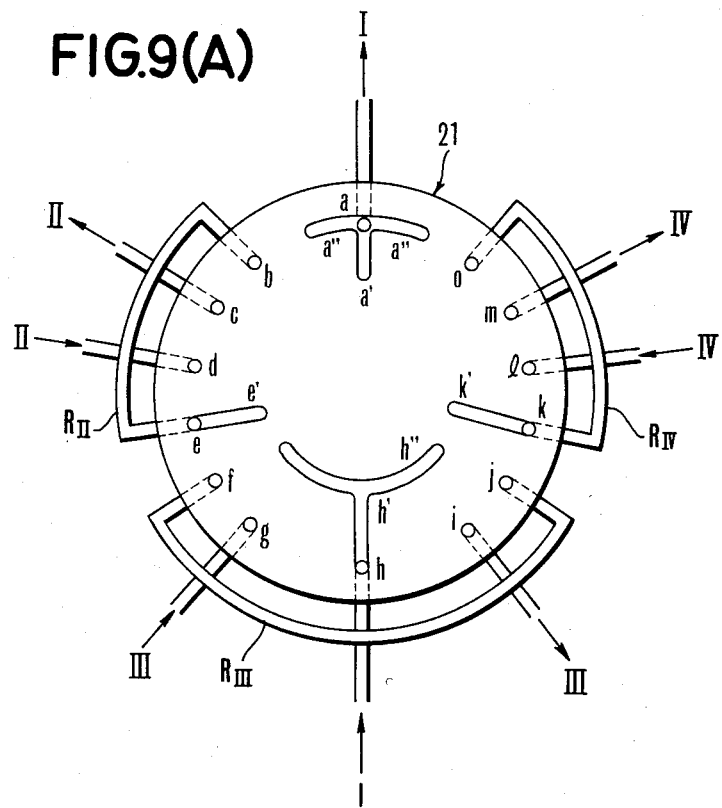
FIGS. 9(A), (B) are front elevations showing the stator and rotor in Example 3.
Figure 9B:
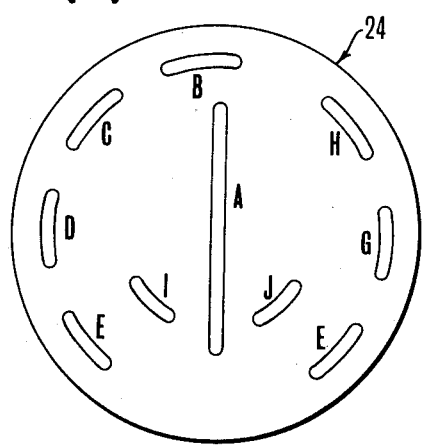

While the Examples 1 and 2 shown in FIGS. 3 through 6 and FIGS. 7 and 8 are for a case when the small openings formed on the stator (or the rotor) are with n=3, they can be made with n=4 or an even larger number of n, and FIG. 9 and FIG. 10 show a case of n=4. FIG. 9(A) shows a stator and FIG. 9(B) shows a rotor, wherein these two are combined, and as a change-over is made between the neutral position and either the normally rotated position (secured by rotating the rotor in the clockwise direction) or the reversely rotated position (secured by a reverse rotation thereof), liquid passing paths will be formed as shown below. The opening h forms an inlet of a first liquid system, and the opening a forms an outlet thereof.

(Neutral position):
First liquid system (I):

$$h \sim h' \to A \to a' - a.$$

The other liquid systems (II, III, IV):
The respective loops are filled.
(Reversely rotated position: in the drawing the rotor is rotated by 20° in the counterclockwise direction)

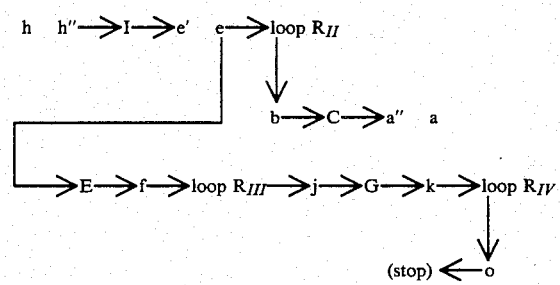

Figure 10A:
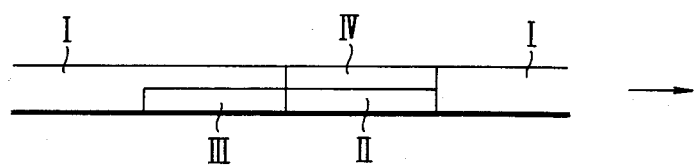
FIGS. 10(A) through (C) explain the modes of liquid injection formed by a positional changeover of the stator and rotor as shown in FIGS. 9.
Figure 10B:
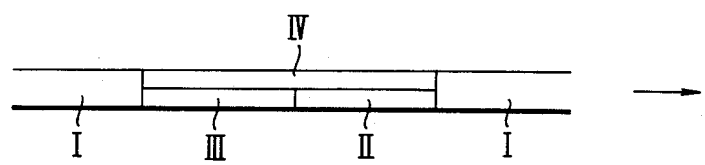

Therefore, the modes of injection for the liquid will be such that, when the loops for each kind of liquid II, III, IV are made to have the same length ($L_{II}=L_{III}=L_{IV}$), the mode of FIG. 10(A) is obtained, and when a condition of $L_{IV}=L_{II}+L_{III}$ exists, the mode of FIG. 10(B) is obtained.

(Normally rotated position):

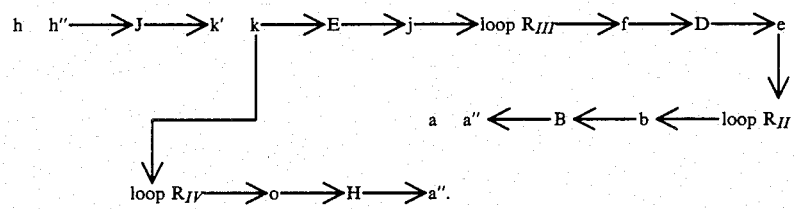

Figure 10C:
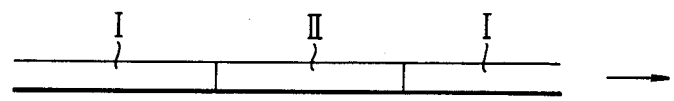

Therefore, the mode of injection for the liquid will be as shown in FIG. 10(C).

Also, the liquid injection at the reversely rotated position in this Example will be useful for an analysis, etc. of sample solutions which require a dilution of liquid or two stage reaction, etc.

EXAMPLE 4

Figure 11A:
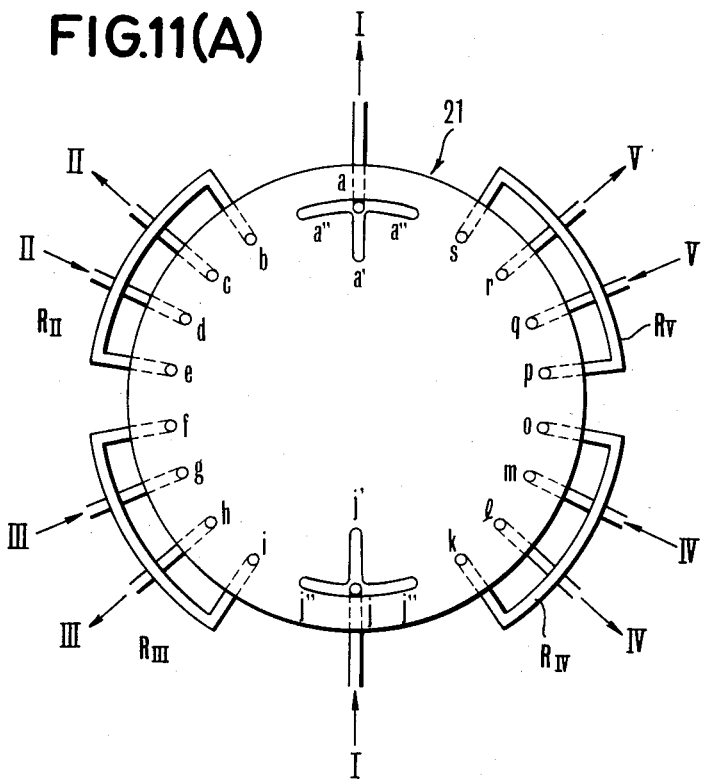
FIG. 11 is a front elevation to show the stator and rotor in Example 4.
Figure 11B:
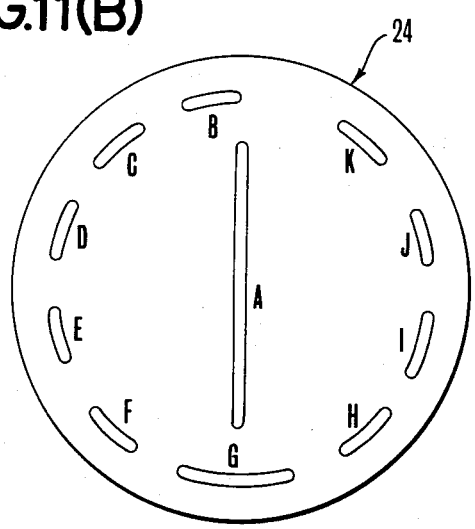

FIG. 11 shows a case in which a similar relationship is made for the liquids, I, II, III, IV, V of n=5. Here, an inlet of the first liquid system is j, and an outlet thereof is a.

(Neutral position):
First liquid system (I):

$$j \sim j' \to A \to a' \sim a$$

The other liquid systems (II, III, IV, V):
The respective loops are filled.
(Reversely rotated position: in the drawing, the rotor is rotated by 16° in the counterclockwise direction):

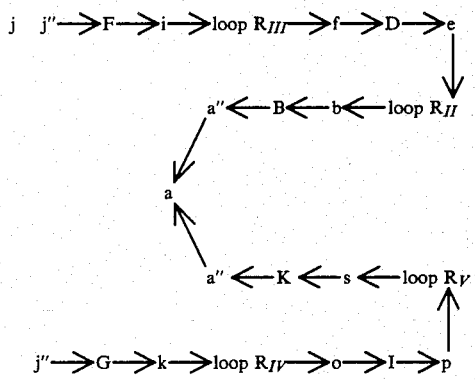

(Normally rotated position):

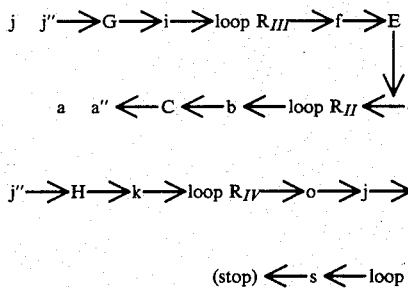

Figure 12A:
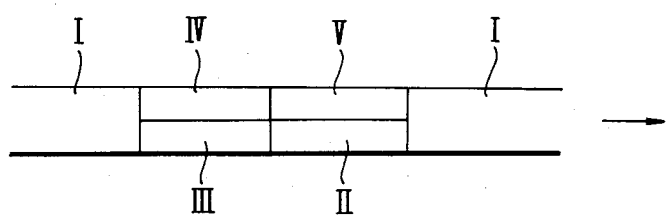
FIG. 12 shows the modes of liquid injection formed by the positional change-over of the stator and rotor as shown in FIG. 11.
Figure 12B:
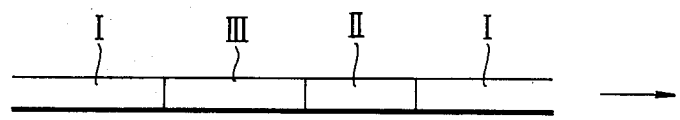
Figure 13:
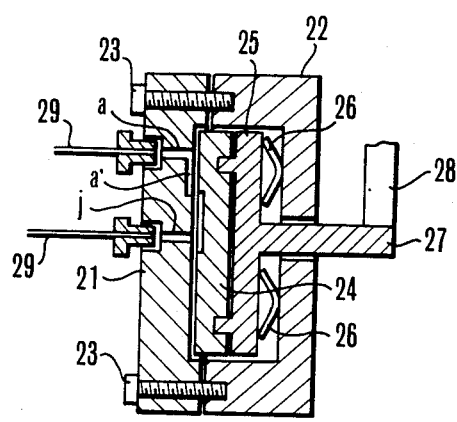
FIG. 13 is a cross-sectional view of the general view of a liquid injection device in Example 5.

The modes for liquid injection in such cases as shown in FIGS. 11(A) and (B) will be as shown in FIG. 12(A) at the reversely rotated position and as shown in FIG. 12(B) at the normally rotated position.

EXAMPLE 5

The example shown below is for a type in which an inlet (or an outlet) is provided at the central position of a disc shaped stator. The example shown in FIG. 13 through FIG. 16 is a liquid injection device with a multi-function of a 3 liquid type used for the analysis of a sample solution, in which the mode to inject a sample solution $S_1$ (second liquid) and a mode to inject a sample solution $S_2$ (third liquid) into the flow of a first liquid can be selected by the normal or reverse rotations of a rotor.

Figure 14A:
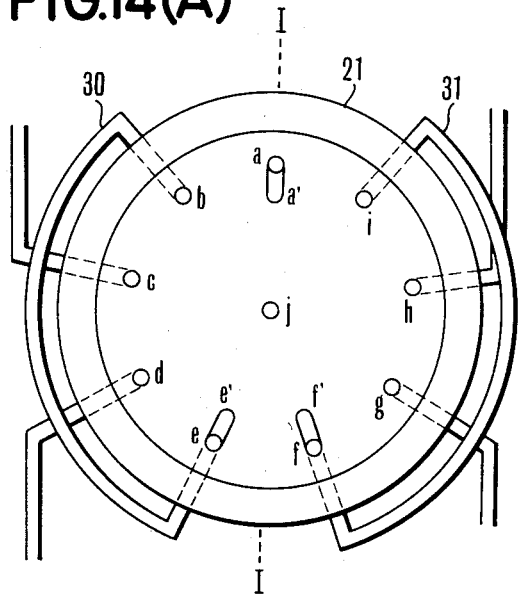
FIG. 14(A) is a front elevation of a stator.
Figure 14B:
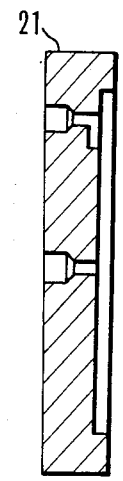
FIG. 14(B) is a cross-sectional view taken along I—I in FIG. 14(A).

The liquid injection device in this example is arranged such that the small opening j out of the small openings a to j on the stator of FIG. 14 is positioned at the center of the circle, and each one of the nine small openings a to i are placed toward the outside of the circle in a positional relationship such that the circle is divided into even angles as shown in the drawing. Also grooves, a~a', e~e', f~f', extending slightly toward the center are provided in association with said small openings a, e and f, respectively.

Figure 15A:
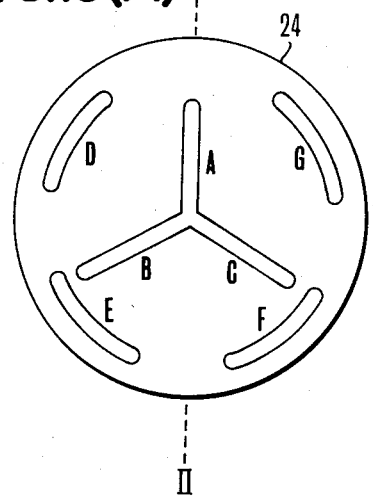
FIG. 15(B) is a cross-sectional view taken along II—II of FIG. 15(A).
Figure 15B:
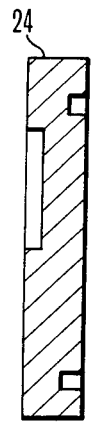

Further, as shown in FIGS. 14 and 15, a plurality of bridging grooves D to G in the circumferential direction, which are intended to selectively connect the small adjacent openings at the stator side (for example the openings a and c for the opening b), and bridging grooves A to C, which are intended to connect the central small opening j and grooves a~a', e~e', f~f' on the stator in a bridge-like manner, are formed on the surface of the rotor 24.

The small openings a to j are similar to those in Example 1 in terms of their association with the external accessory equipment and are arranged in the following manner. That is, the opening j is an outlet for an eluant which is arranged so as to be selectively connected to paths for use in a flow injection analysis method or for a liquid chromatography analysis. The opening a is an inlet for an eluant T and is connected to an eluant tank through a pump P (neither one thereof is shown in the drawing). The openings b and e are connected to both ends 30 of the specimen loop 30 of a sample solution $S_1$. Also, f and i at symmetrical positions thereto are connected to both ends of the specimen 31. The openings c and d form two points within a filling circuit for the sample solution $S_1$. The opening C is connected to the specimen vessel 32, while the opening d is connected to a suction pump (not shown in the drawing). Similarly, h and g at symmetrical positions thereto are arranged in such a way that h is connected to the specimen vessel 33 within a filling circuit for the sample solution $S_2$, while g is connected to a suction pump (not shown in the drawing).

Figure 16A:
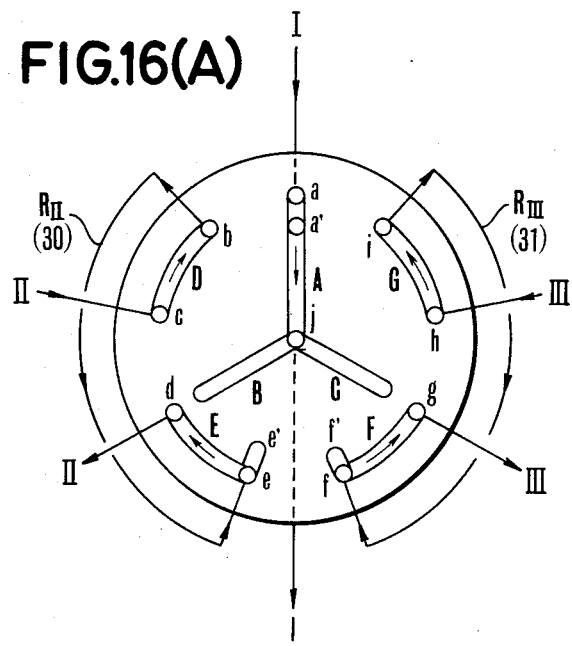
FIGS. 16 (A) through (C) show states of forming the liquid passing paths accompanying a positional change-over of the stator and rotor in Example 5.
FIGS. 16(D), (E) show the states of liquid injection.

FIG. 16(A) shows a state in which the matched position of the stator and the rotor is made at the neutral position, which is for the liquid filling mode and constitutes a basic position of this liquid injection device.

Since the bridging groove A directed radially from the point j on the rotor side has its position matched with grooves a~a' on the stator under this state, the small openings a and j form a liquid passing path of a~a'→A→j, and the eluant forms a normal flow by the pump P.

Also, the small openings b, c, d and e of a sample solution $S_1$ system form a liquid passing path of c→D→b→loop 30→e→E→d by means of the bridging grooves D and E in the circumferencial direction. Thus the specimen loop 30 is filled with the sample solution $S_1$ from the specimen vessel 32.

Similarly, the specimen loop 31 is filled with $S_2$ by a liquid passing path of h→G→i→loop 31→f→F→g in a sample solution $S_2$ system.

Figure 16B:
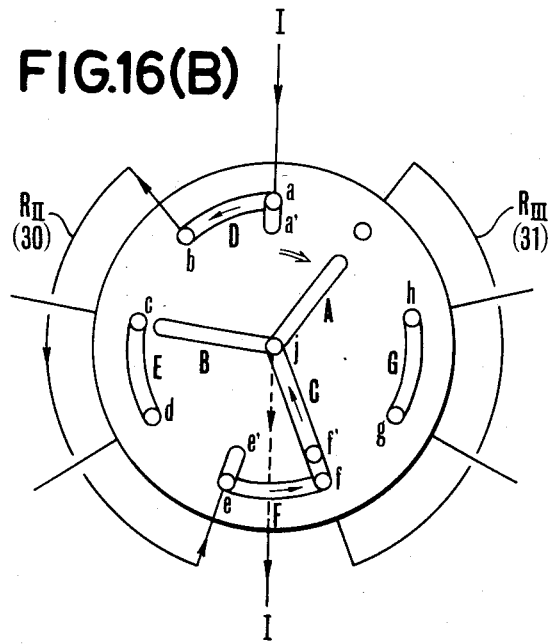

FIG. 16(B) shows a state in which the rotor 24 in FIG. 16(A) is rotated slidingly against the stator 21 by a predetermined angle (360°/9) in the clockwise direction and is changed over to a normally rotated position. The liquid passing path is changed by the rotation. That is, the bridging groove A (which had its position matched with the groove a~a' on the stator), is now released, and the bridging groove C now has its position matched with the groove f~f' on the stator. Also, as the result of this rotation, the connections among the small openings b through f in the sample solution $S_1$ system will change in relation to the bridging of the grooves D, E and F in the circumferential direction as follows. That is, D connects the small openings a and b in the stator, E connects the small openings c and d, F connects the small openings e and f, and G connects the small openings g and h. Therefore, the liquid passing path is formed between the inlet a and the outlet j of the eluant in the following manner:

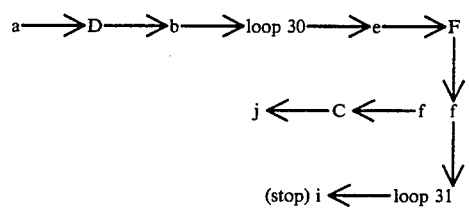

Figure 16C:
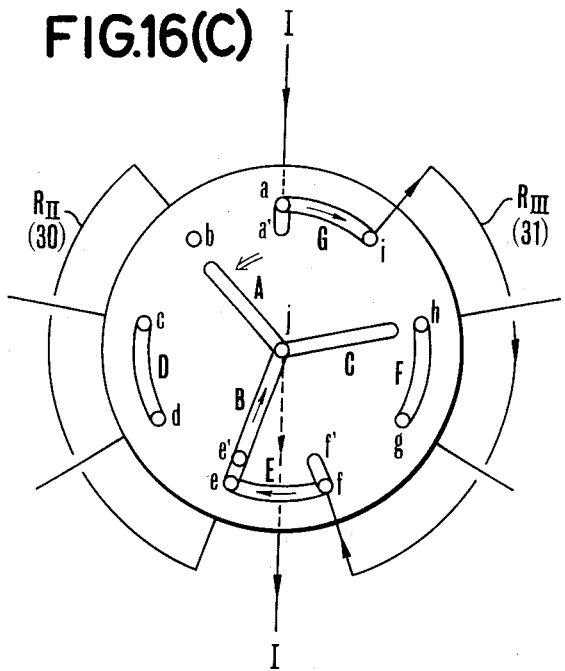
Figure 16D:
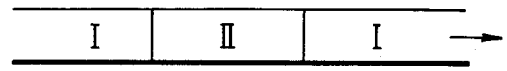

That is, as a result, the sample solution $S_1(II)$ within the specimen loop 30, is injected into the eluant $T(I)$, and thus an injection of the sample solution $S_1$ into the eluant I as a "plug flow" (refer to FIG. 16(D) ) in a liquid injection mode at the normally rotated position is attained.

FIG. 16(C) shows another injection mode in which the rotor 24 in FIG. 16(A) is rotated against the stator 21 in the counterclockwise direction (reverse rotation) and is changed over to the reversely rotated position. As a result of the rotation, the liquid passing path is changed in a manner similar to that in the case of FIG. 16(B).

That is, a direct connection of the eluant through the bridging groove A is shut off, and a connection for liquid between the inlet a and the outlet j of the eluant will be as shown below:

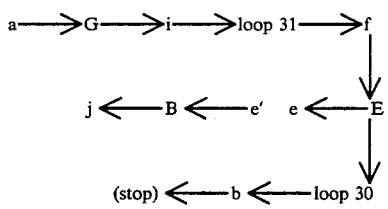

Figure 16E:
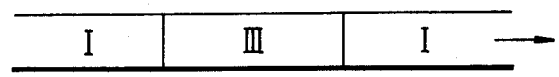

Thus as a result, the sample solution $S_2(III)$, within the specimen loop 31 only, is injected into the eluant $T(I)$ in an injection mode at the reversely rotated position, and thus the injection of the sample solution $S_2$ into the eluant T (I) as a "plug flow" (refer to FIG. 16(E) ) is attained.

Also, regarding the above explanations, the lengths of the bridging grooves A to G, the positioning of the small openings a to j, the lengths of grooves on the stator, and the angle of change-over of the rotor from its neutral position to the normally and reversely rotated positions are naturally to be set in correspondence to the above-mentioned operations.

EXAMPLE 6

FIGS. 17(A) through (E) show a device in which the columns 12 and 14 are provided in an intervening manner at the loop parts. The rest of the device is similar to the preceeding example. The eluant is sent to the small opening a through a pump and is then connected to a detector (not shown in the drawing) through the small opening j.

Figure 17A:
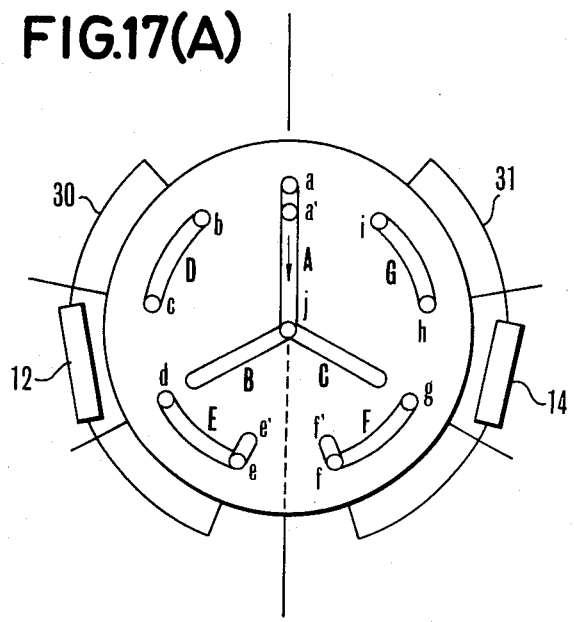
FIGS. 17(A) through (C) show states of a positional change-over of the stator and rotor in the case of a column operation as in Example 6.

FIG. 17(A) shows the neutral position in which a liquid passing path, a~a'~A~j is formed, thus providing a flow of the eluant such that it does not pass through either one of the columns.

Figure 17B:
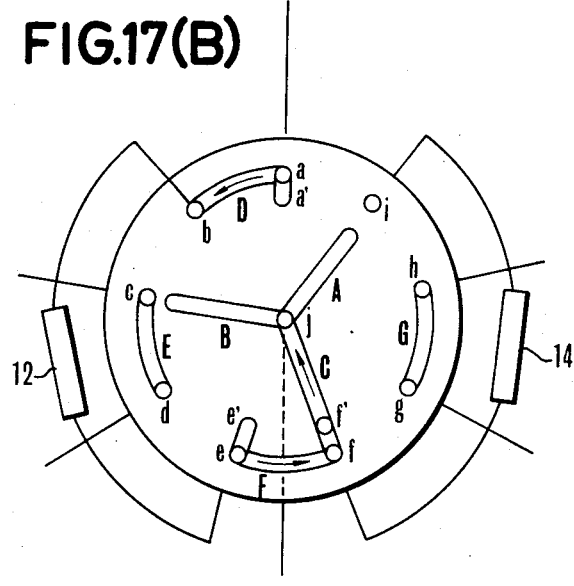

FIG. 17(B) shows a state in which the rotor 24 shown in FIG. 17(A) is rotated against the stator 21, by 40° in the normal direction. As a result of this rotation, the connection for the liquid is made through a→D→b-→column 12→e→F→f~f'→C→j, thus forming a flow of the eluant in which the column 12 is selected as shown in FIG. 17(D).

Figure 17C:
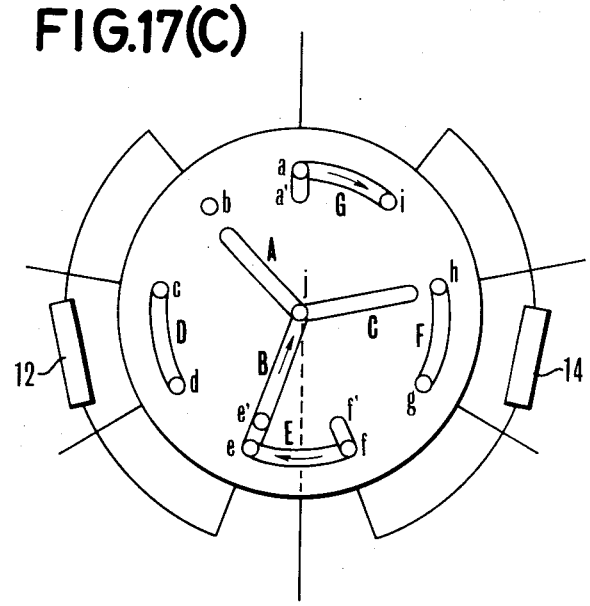
Figure 17D:
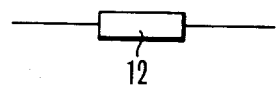
FIGS. 17(D), (E) show the columns selected in liquid injection.
Figure 17E:
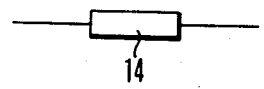

Also, FIG. 17(C) shows a state in which the rotor 24 shown in FIG. 17(A) is rotated the stator 21, by 40° in the reverse direction. As a result of this rotation, the connection for the liquid is made through a→G→i→ column 14→f→E→e~e'→B→j, thus forming a flow of the eluant in which the column 14 is selected as shown in FIG. 17(E).

Also, a prescribed buffer liquid is made to flow to the columns 12 and 14 at the neutral position as shown in FIG. 17(A).

EXAMPLES 7 AND 8

Figure 18A:
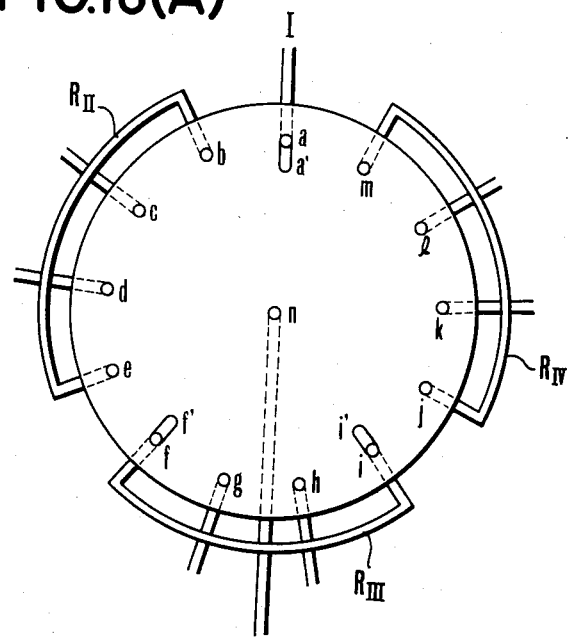
FIGS. 18 to 37 show Example 7 through 16, wherein each (A) figure of FIGS. 18, 20, 22, 24, 26, 28, 30, 32, 34 and 36 is a front elevation of the stator in the respective example, while each (B) figure of the same shows a front elevation of the rotor in each example. And each one of figures (A) through (C) of FIGS. 19, 21, 23, 25, 27, 29, 31, 35 and 37 show states of forming the liquid passing paths accompanying positional change-over of a stator and a rotor in each example. Figures (D), (E) in the same show states of liquid injection in each example.
Figure 20A:
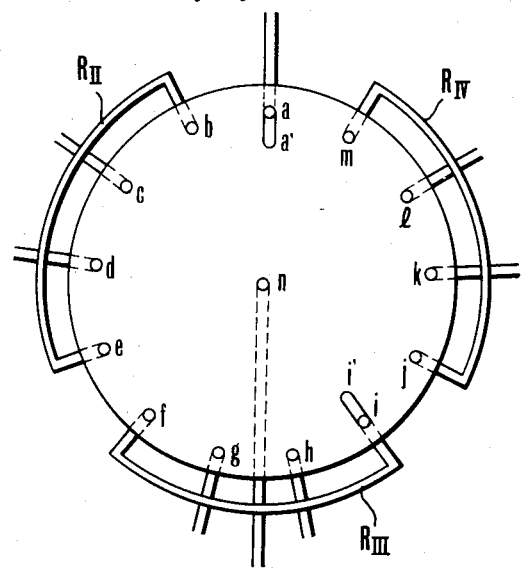

FIGS. 18(A) and (B) show an example of a case in which the number n of the liquid is 4 (Example 7). FIGS. 20(A) and (B) show a case in which the number n of the liquid is similarly 4. However, at the same time the structure in Example 7 is somewhat modified to change the injection modes of liquid (Example 8).

Figure 20B:
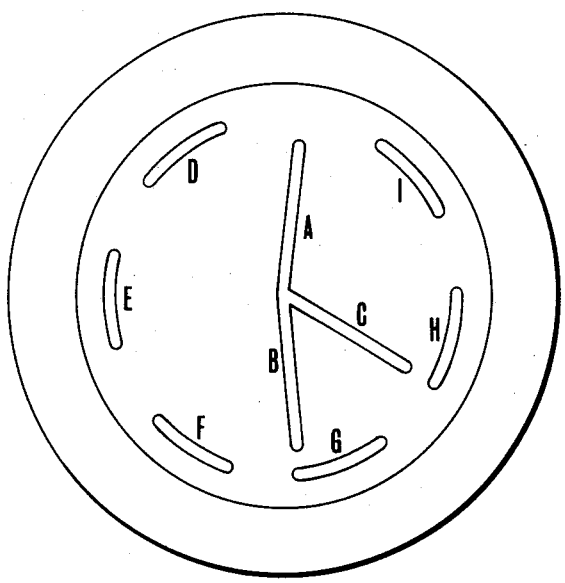

Example 8 in FIGS. 20 has a basically similar arrangement to that of Example 7 except that the number n of liquid used is increased by one and a selective system is employed such that a choice of whether the liquid to be injected as a "plug flow" be II and III or III and IV can be selected. Further, the numbers of the small openings and bridging grooves are increased (this will be same in the succeeding examples).

Figure 18B:
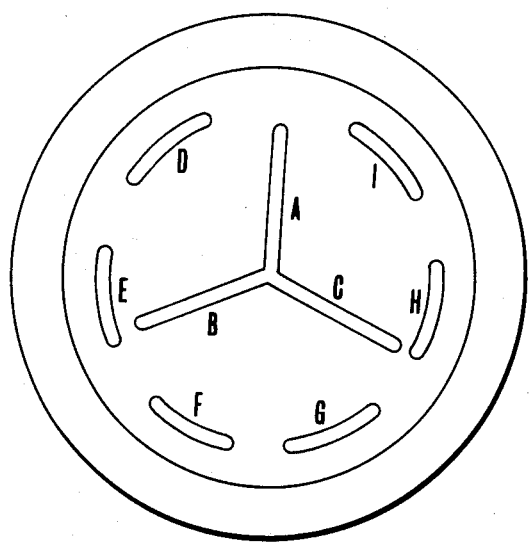

A liquid filling mode and a liquid injection mode comprising combinations of the stator and the rotor as shown in FIGS. 18(A) and 18(B) are made up in the manner shown below:

(Neutral position: liquid filling mode):

First liquid system: a   a'──→A──→n

The other liquid systems (II, III, IV):
Each loop is filled respectively.
(Refer to FIG. 19(A))

(Normally rotated position: liquid injection mode. The rotor is rotated clockwise by 27.7°)

a   a'─→D─→b─→$R_{II}$─→e─→F─→f─→$R_{III}$ n←─C←─i   i'

(stop)←─m←─$R_{IV}$←─j←─H (Refer to FIG. 19(B))

(Reversely rotated position: liquid injection mode. The rotor is rotated counterclockwise by 27.7°)

a   a'─→I─→m─→$R_{IV}$─→j─→G─→i   i' n←─B←─f   f'←─$R_{III}$ (stop)←─b←─$R_{II}$←─e←─E (Refer to FIG. 19(C))

Figure 19D:
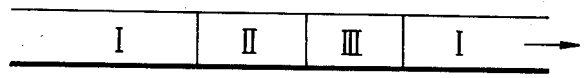
Figure 19E:
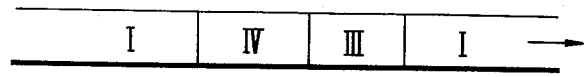

In these cases, the mode of liquid injection will be as shown in FIG. 19(D) at the normally rotated position, and it will be as shown in FIG. 19(E) at the reversely rotated position.

In Example 8 shown in FIGS. 20, a selection system is employed such that a choice is made as to whether the liquid to be injected as a "plug flow" comprises II, III or only IV, and the liquid filling mode and a liquid injection mode thereof at the three positions as in FIGS. 19 of Example 7 will be as follows:

(Neutral position: liquid filling mode)

First liquid system: a   a'──→A──→n

The other liquid systems (II, III, IV):
Each loop is filled respectively.
(Refer to FIG. 21(A))

Figure 21D:
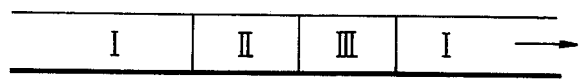
Figure 21E:
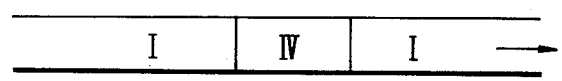
Figure 21A:
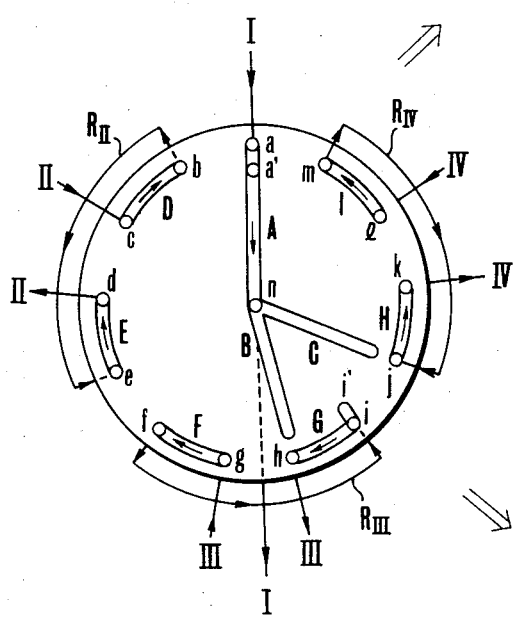
Figure 21B:
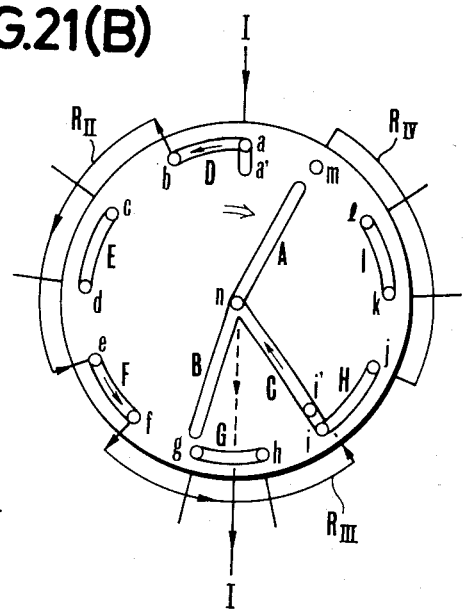

(Normally rotated position: liquid injection mode. The rotor is rotated counterclockwise by 27.7°)

a   a'─→D─→b─→$R_{II}$─→e─→F─→f n←─C←─i'   i←─$R_{III}$ (stop)←─m←─$R_{IV}$←─j←─H (Refer to FIG. 21(B))

Figure 21C:
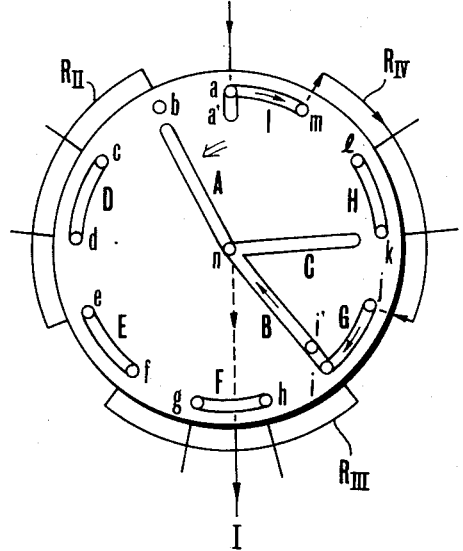

(Reversely rotated position: liquid injection mode. The rotor is rotated counterclockwise by 27.7°)

a   a'─→I─→m─→$R_{IV}$─→j─→G n←─B←─i'   i (stop)←─b←─$R_{II}$←─e←─E←─f←─$R_{III}$ (Refer to FIG. 21(C))

In these cases, the mode of liquid injection will be as shown in FIG. 21(D) at the normally rotated position, and will be as shown in FIG. 21(E) at the reversely rotated position.

The Examples 5, 6, 7 and 8 shown above refer to a case wherein the small openings provided in the stator (or the rotor) are positioned on the outer portion of a circle in the circumferential direction.

EXAMPLE 9

Example 9 shown in FIG. 22 and FIG. 23 refers to a case wherein the small openings are formed as two concentric circles, wherein each liquid supply path at the three positions will be as shown below:

(Neutral position: liquid filling mode)

First liquid system: f   f'⟶B⟶m

The other liquid systems (II, II):
Each loop is filled respectively.
(Refer to FIG. 23(A))

(Normally rotated position: liquid injection mode. The rotor is rotated clockwise by 60°)

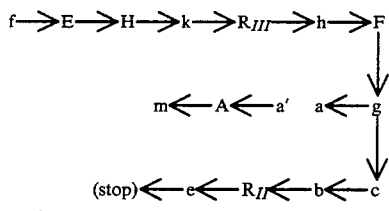

Figure 23A:
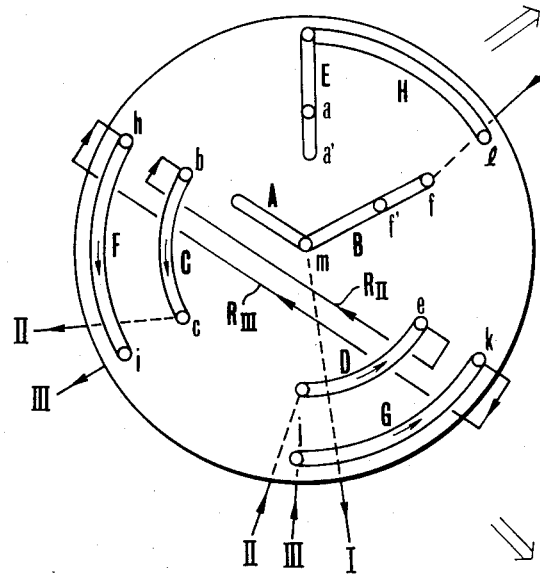
Figure 23B:
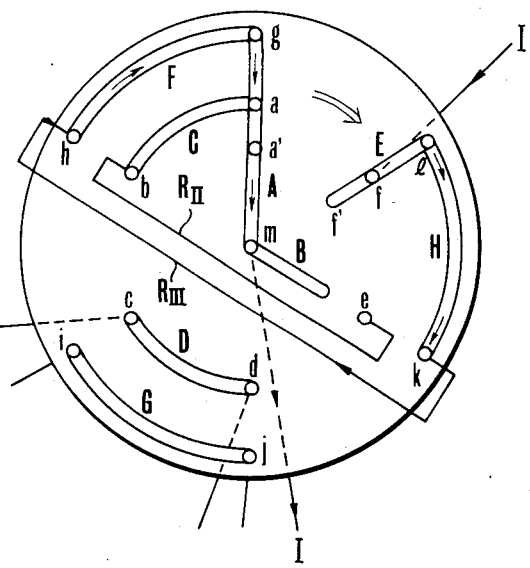

(Refer to FIG. 23(B))

(Reversely rotated position: liquid injection mode. The rotor is rotated counterclockwise by 60°)

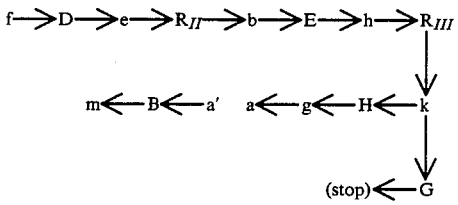

Figure 23C:
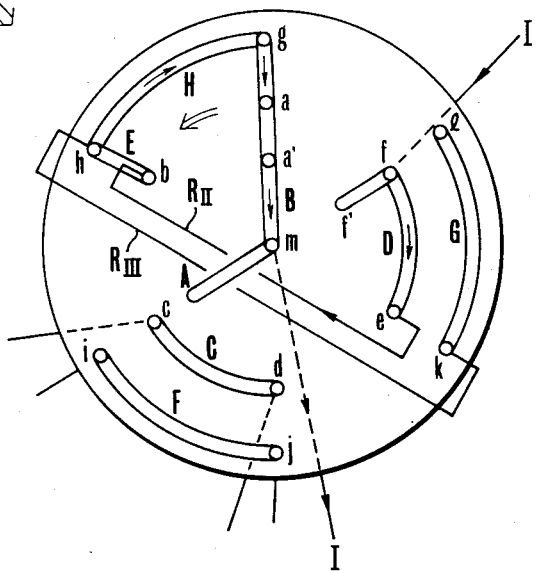

(Refer to FIG. 23(C))

Figure 22A:
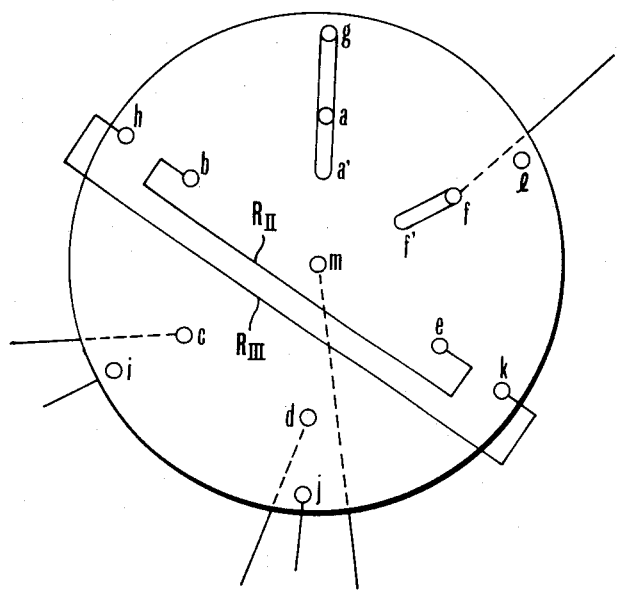
Figure 22B:
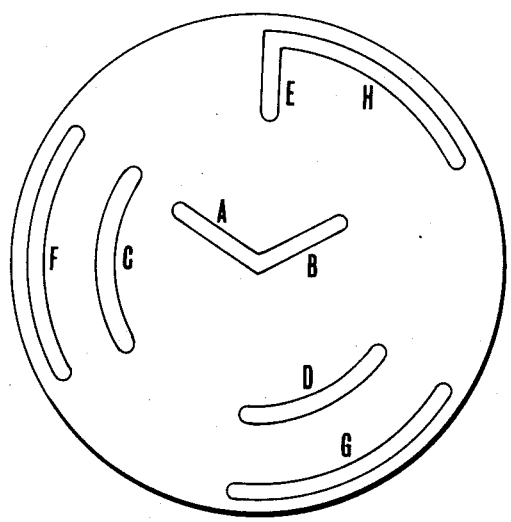
Figure 23D:
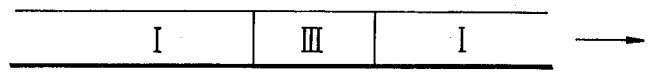
Figure 23E:
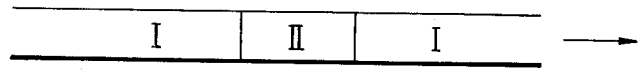

The modes of injection of the liquid in the cases of FIGS. 22(A) and 22(B) will be as shown in FIG. 23(D) at a normal rotation, and will be as shown in FIG. 23(E) at a reverse rotation.

EXAMPLE 10

The example shown in FIG. 24 and FIG. 25 shows a case wherein small openings in the stator are formed as three concentric circle, and each liquid passing path at the three positions is formed in the following manner:

(Neutral position: liquid filling mode)

First liquid system: f   f'⟶B⟶S

The other liquid systems (II, III, IV):
Each loop is filled respectively.
(Refer to FIG. 25(A))

(Normally rotated position: liquid injection mode. The rotor is rotated clockwise by 60°)

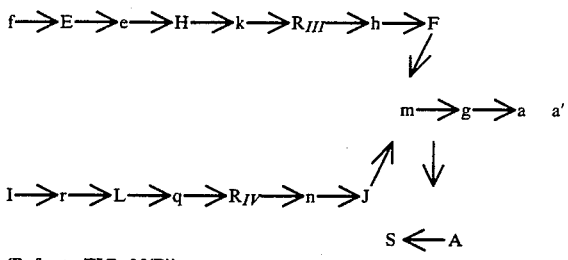

(Refer to FIG. 25(B))

(Reversely rotated position: liquid injection mode. The rotor is rotated counterclockwise by 60°)

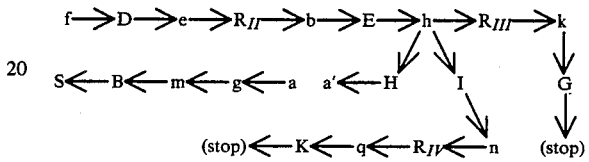

(Refer to FIG. 25(C))

Figure 25D:
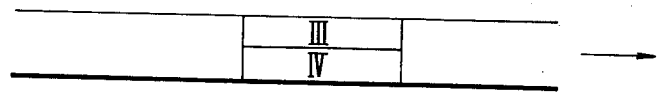
Figure 25E:
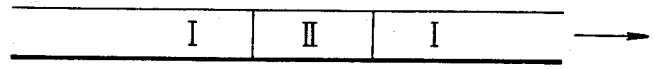
Figure 24A:
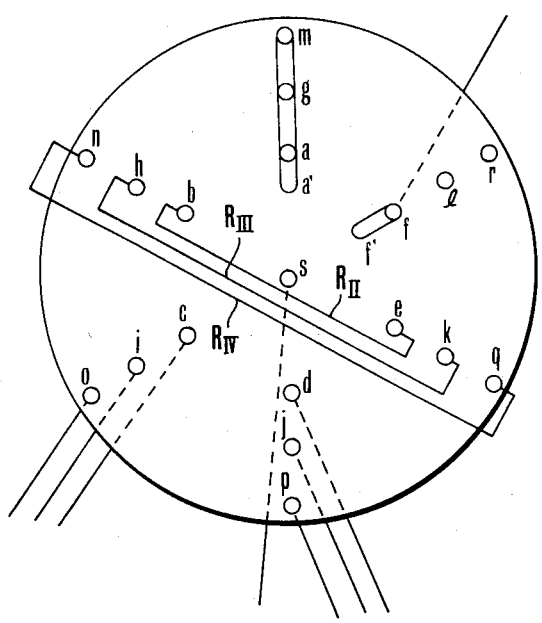
Figure 24B:
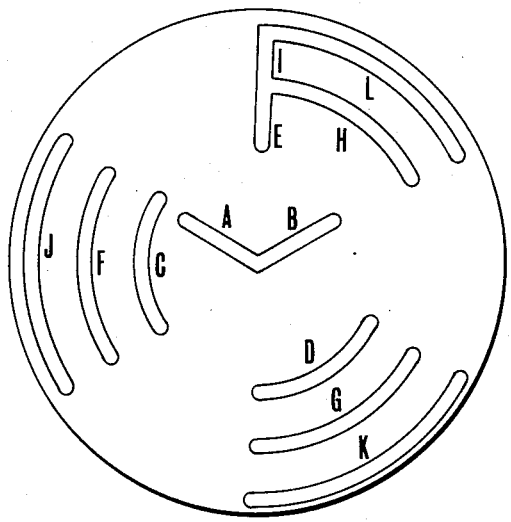

The mode of injection of liquid in the case of FIGS. 24(A) and 24(B) will be as shown in FIG. 25(D) at a normal rotation, and it will be as shown in FIG. 25(E) at a reverse rotation.

EXAMPLE 11

Example 11 shown in FIG. 26 and FIG. 27 shows a liquid injection device of a sample solution analysis type in which a mode to inject a sample solution S (second liquid (II)) only into the flow of a first liquid (I) and a mode to simultaneously inject the sample solution S and a reagent R; (third liquid (III)) are selected by either the normal or reverse rotation of the rotor.

Figure 26A:
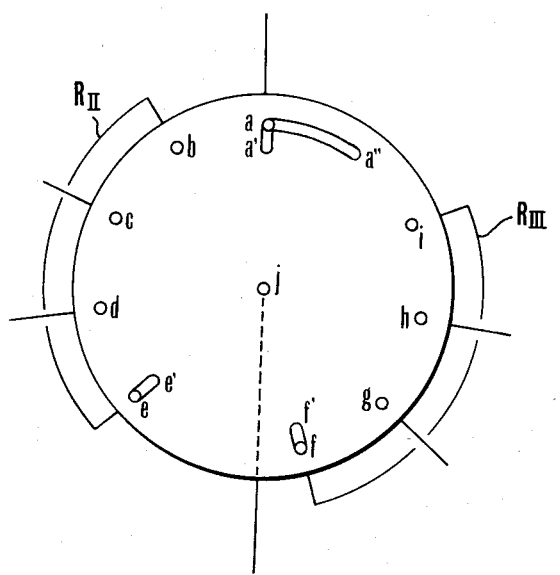
Figure 26B:
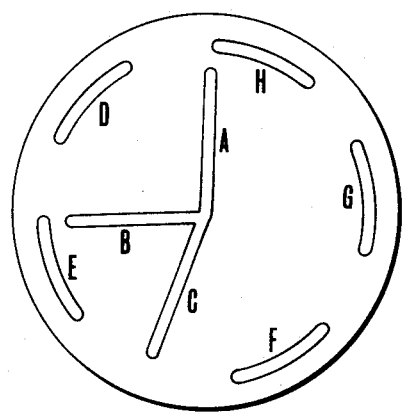

FIG. 26(A) shows a stator, and FIG. 26(B) shows a rotor as in the preceeding examples. A mode of injection of only a sample solution S (in the normally rotated position) and a mode to inject the sample solution S and a reagent R in a "merging zone" type in this example will be as shown below:

(Neutral position: liquid filling mode)

First liquid system (I): a   a'⟶A⟶j

The other liquid systems (II, III):
Each loop is filled respectively.
(Refer to FIG. 27(A))

(Normally rotated position: sample solution S injection mode:
The rotor is rotated clockwise by 32.7°)

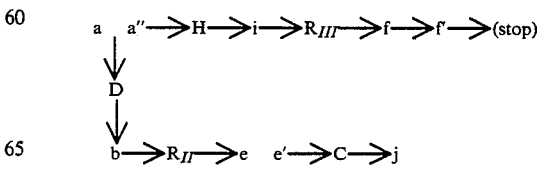

(Refer to FIG. 27(B))

(Reversely rotated position: sample solution S and reagent R injection mode.
The rotor is rotated counterclockwise by 32.7°)

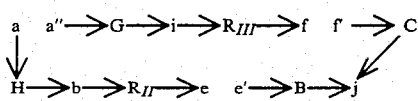

(Refer to FIG. 27(C))

Figure 27D:
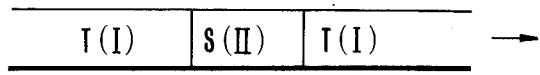
Figure 27E:
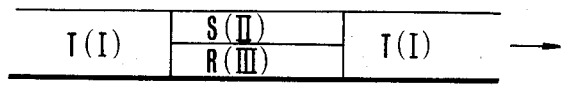

Therefore, only the sample solution S (II) will be injected at the normally rotated position as shown in FIG. 27(D), and the sample solution S (II) and the reagent R (III) are injected in a "merging zone type" as shown in FIG. 27(E).

EXAMPLE 12

Example 12 shown in FIG. 28 and FIG. 29 is to form liquid passing paths for 4 kinds of liquids in the manner as shown below by a change-over to three positions.

(Neutral position: liquid filling mode)

First liquid system (I): a  a'———>A———>n

The other liquid systems (II, III, IV):
Each loop is filled respectively.
(Refer to FIG. 29(A))

(Normally rotated position: liquid injection mode.
The rotor is rotated clockwise by 34°)

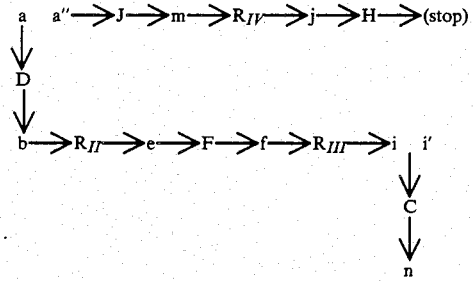

Figure 29D:
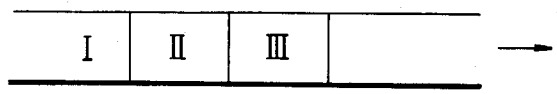
Figure 29E:
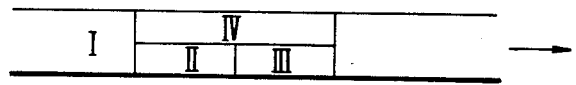
Figure 29A:
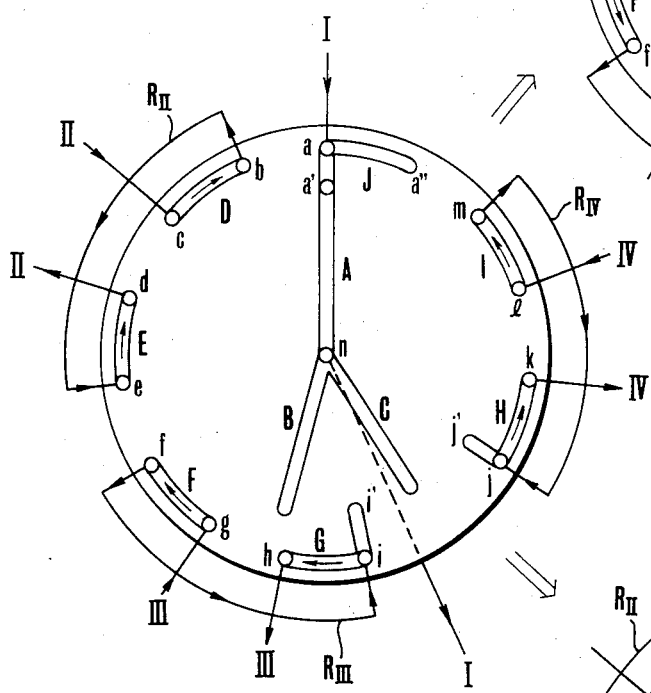
Figure 29B:
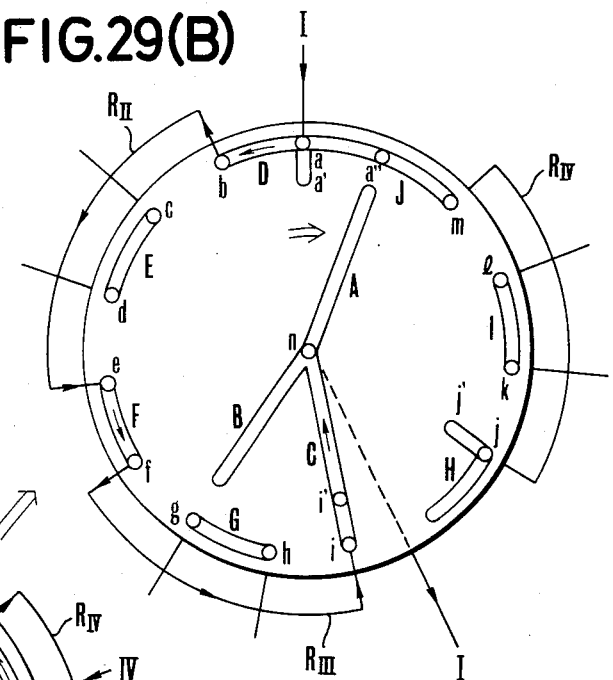

(Refer to FIG. 29(B))

(Reversely rotated position: liquid injection mode.
The rotor is rotated counterclockwise by 34°)

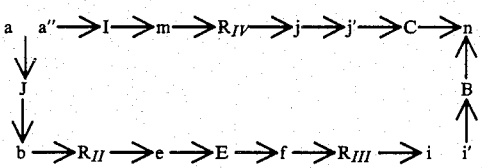

Figure 29C:
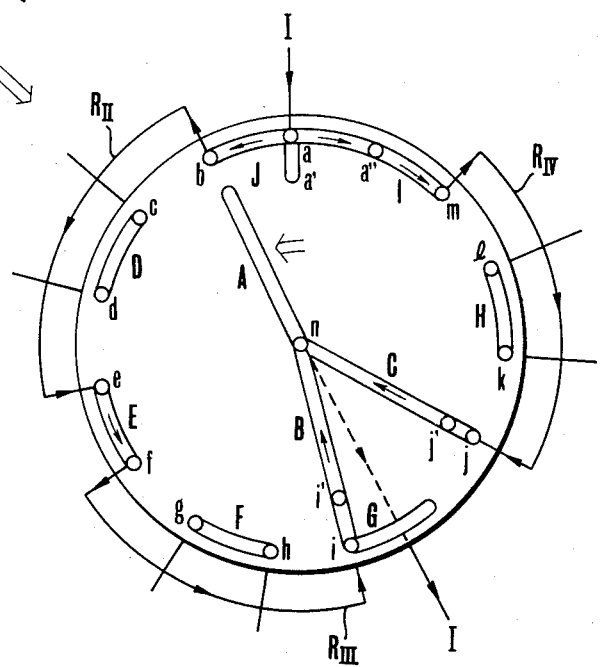

(Refer to FIG. 29(C))

Figure 28A:
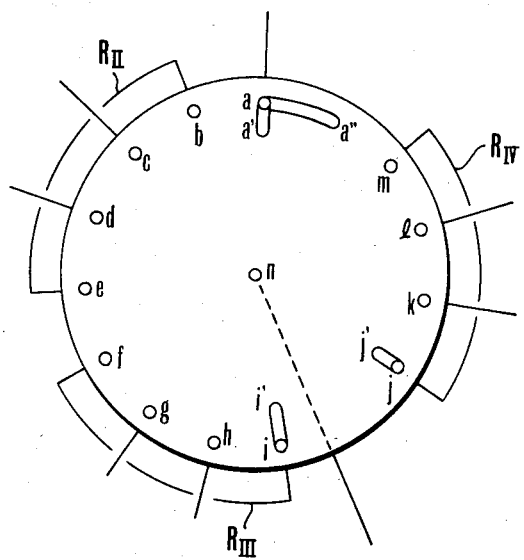
Figure 28B:
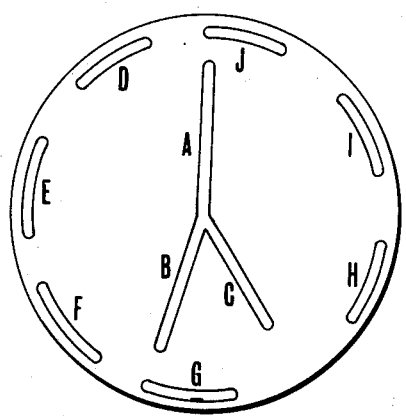

Therefor the mode of injection of the liquid in the case of FIGS. 28(A) and 28(B) will be as shown in FIG. 29(D) in a normal rotation, and it will be as shown in FIG. 29(E) in a reverse rotation.

EXAMPLE 13

Example 13 shown in FIG. 30 and FIG. 31 shows a case wherein the small openings on the stator are formed as two concentric circles, and each liquid passing path at each of three positions is formed in the manner shown below:

(Neutral position: liquid filling mode)
First liquid system (I):

l———>J———>g———>a  a'———>A———>m

The other liquid systems (II, III):
Each loop is filled respectively.
(Refer to FIG. 31(A))

(Normally rotated position: liquid injection mode.
The rotor is rotated clockwise by 60°)

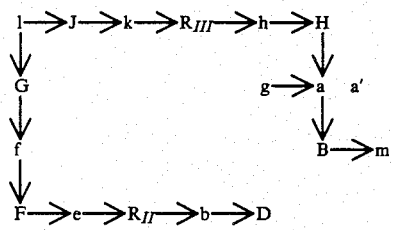

(Refer to FIG. 31(B))

(Reversely rotated position: liquid injection mode.
The rotor is rotated counterclockwise by 60°)

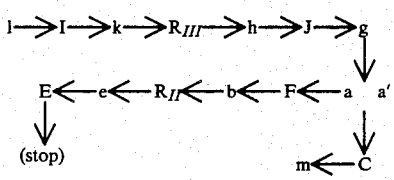

(Refer to FIG. 31(C))

Figure 30A:
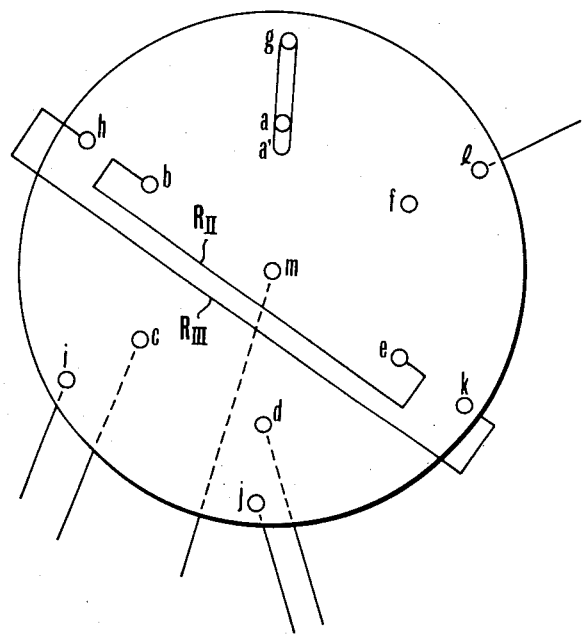
Figure 30B:
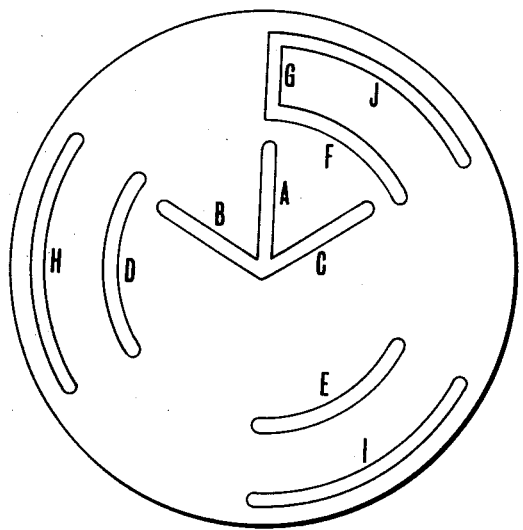
Figure 31D:
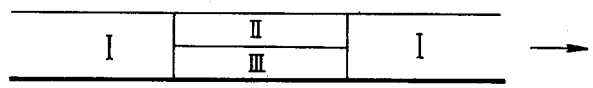
Figure 31E:
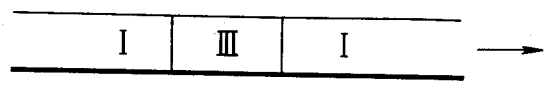

Therefore, the mode of injection of the liquid in the case of FIGS. 30(A) and 30(B) will be as shown in FIG. 31(D) in a normal rotation, and it will be as shown in FIG. 31(E) in a reverse rotation.

EXAMPLE 14

Example 14 shown in FIG. 32 and FIG. 33 shows a case wherein small openings at the stator are formed as three concentric circles, and a liquid passing path at each one of three positions is formed in the manner shown below:

(Neutral position: liquid filling mode)
First liquid system (I):

s———>N———>m———>K———>g———>G———>a  a'———>A———>t

The other liquid systems (I, II, IV):
Each loop is filled respectively.
(Refer to FIG. 33(A))

(Normally rotated position: liquid injection mode.
The rotor is rotated clockwise by 60°)

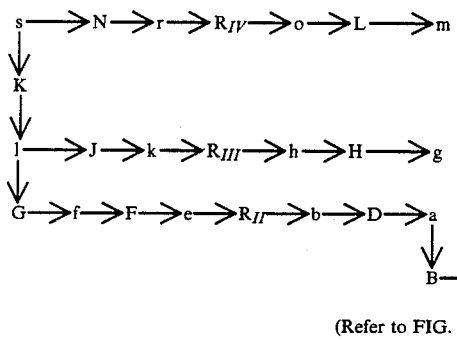

Figure 33D:
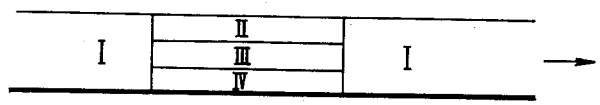
Figure 33E:
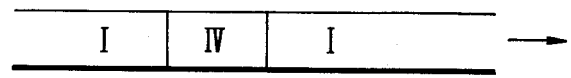
Figure 33A:
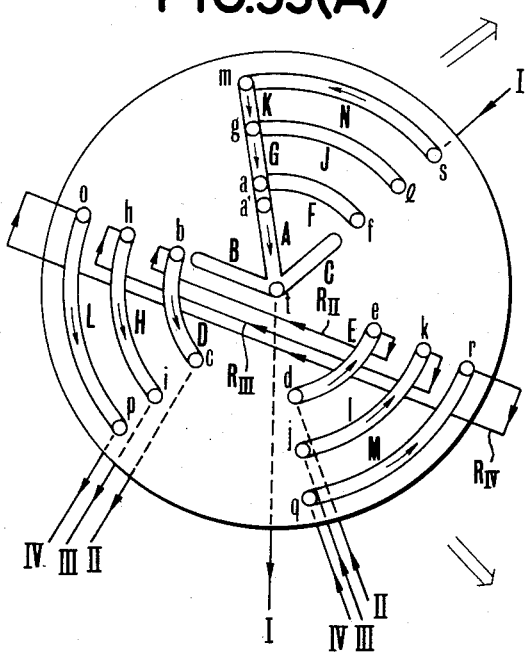
Figure 33B:
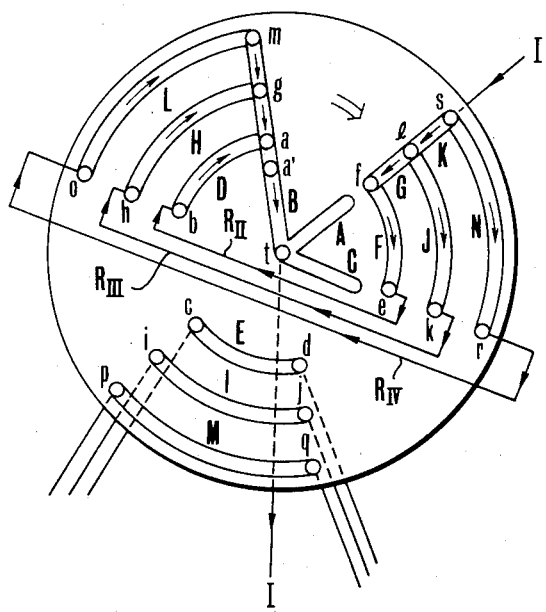

(Refer to FIG. 33(B))

(Reversely rotated position: liquid injection mode.
The rotor is rotated counterclockwise by 60°)

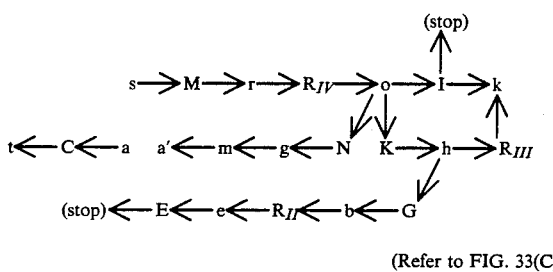

Figure 33C:
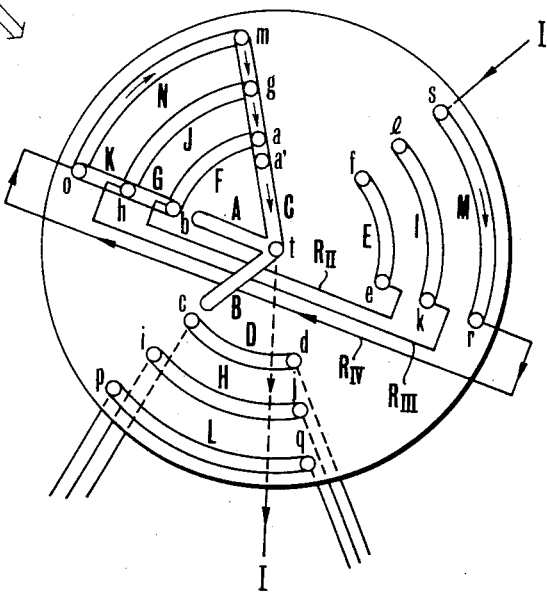

(Refer to FIG. 33(C))

Figure 32A:
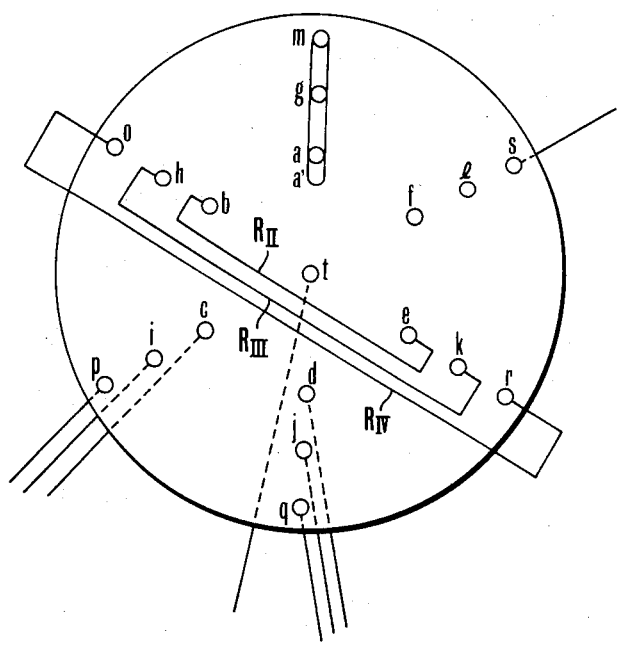
Figure 32B:
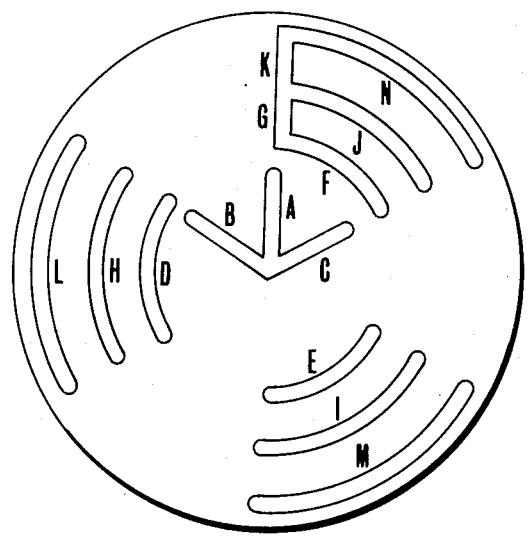

Therefore, the mode of injection of the liquid in the case of FIGS. 32(A) and 32(B) will be as shown in FIG. 33(D) in a normal rotation, and it will be as shown in FIG. 33(E) in a reverse rotation.

EXAMPLE 15

Example 15 shown in FIG. 34 and FIG. 35 shows a liquid injection device of a sample solution analysis type in which the order of injection of a sample solution $S_1$ (second liquid II) and a sample solution $S_2$ (third liquid III) which are simultaneously injected into the flow of a first liquid (I) can be changed and selected depending on the rotation of the rotor to either a normally rotated position or a reversely rotated position. Formation of the liquid passing paths at each one of three positions is done in the manner shown below. In this Example, the small openings on the stator are provided as two concentric circles.

(Neutral position: liquid filling mode)

First liquid system (I): f    f→A→m
The other liquid systems (II, III):
Each loop is filled respectively.

(Refer to FIG. 33(A))

(Normally rotated position: liquid injection mode.
The rotor is rotated clockwise by 60°)

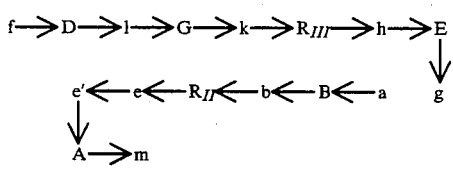

Figure 35A:
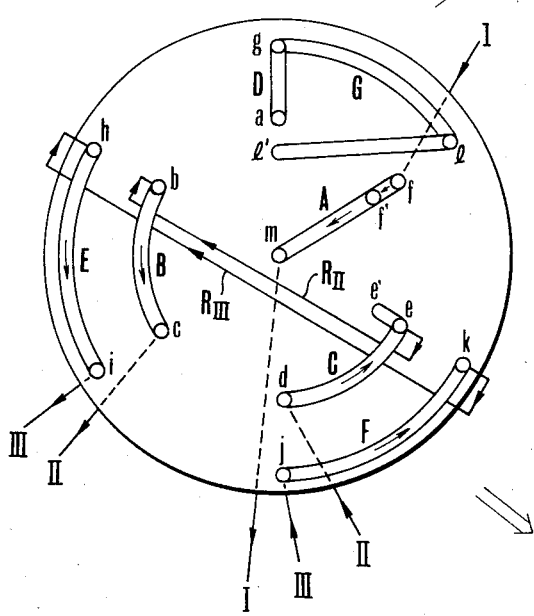
Figure 35B:
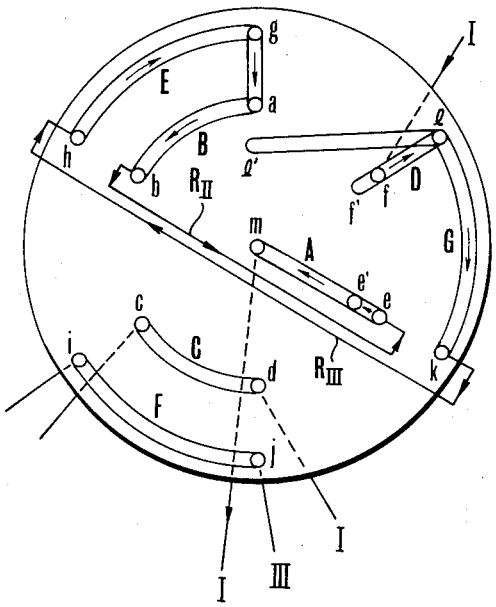

(Refer to FIG. 35(B))

(Reversely rotated position: liquid injection mode.
The rotor is rotated counterclockwise by 60°)

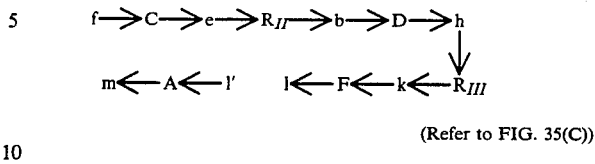

Figure 35C:
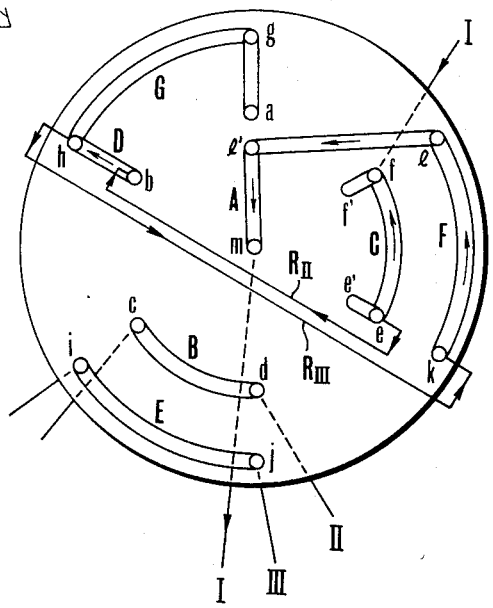

(Refer to FIG. 35(C))

Figure 34A:
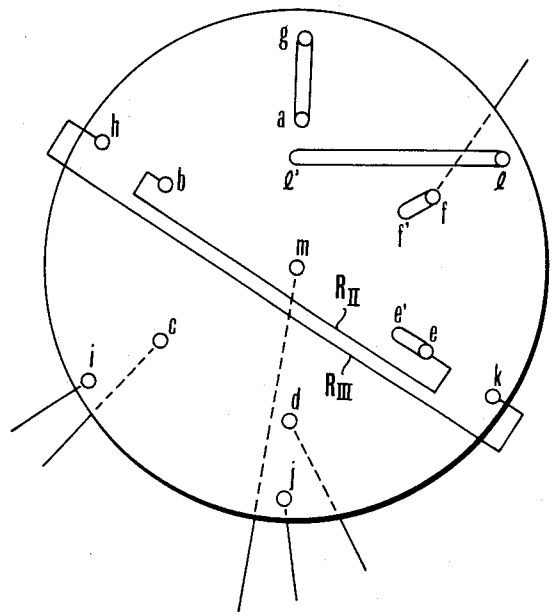
Figure 34B:
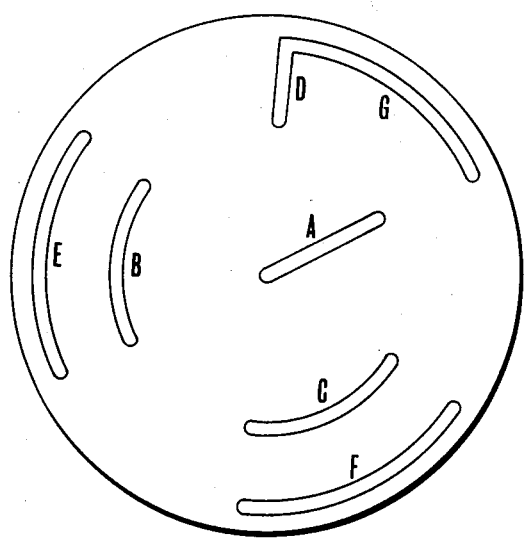
Figure 35D:
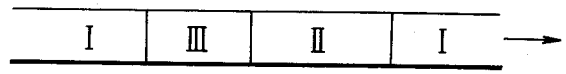
Figure 35E:

Therefore, the mode of injection of the liquid in the case of FIGS. 34(A) and 34(B) will be as shown in FIG. 35(D) in a normal rotation, and it will be as shown in FIG. 35(E) in a reverse rotation.

EXAMPLE 16

Example 16 shown in FIG. 36 and FIG. 37 shows a case wherein one more liquid system is provided than in Example 15 (that is, h=4), with the small openings on the stator being provided as three concentric circles. Formation of the respective liquid passing paths at the three positions are made in the manner shown below:

(Neutral position: liquid filling mode)

First liquid system (I): a    a'→A→s
The other liquid systems (II, III, IV):
Each loop is filled respectively.

Figure 37D:
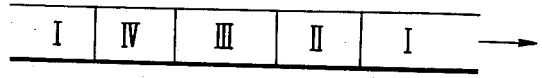
Figure 37E:
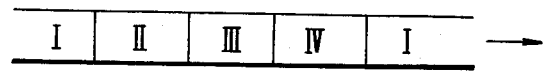
Figure 37B:
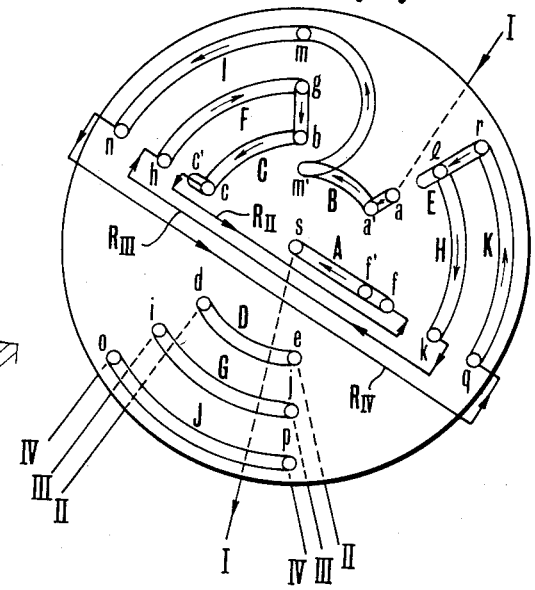
Figure 37A:
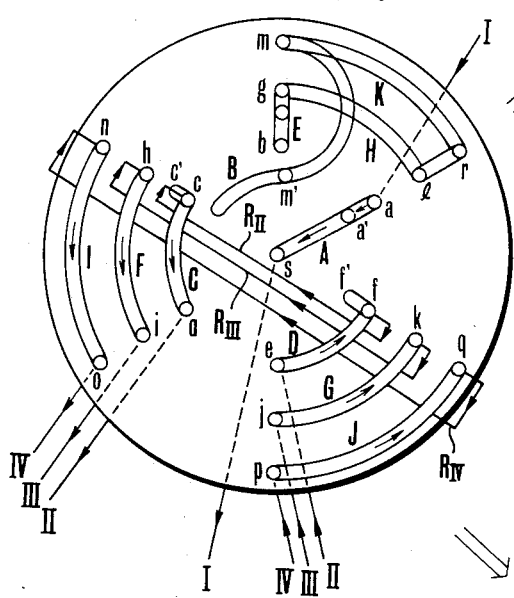

(Refer to FIG. 37(A))

(Normally rotated position: liquid injection mode.
The rotor is rotated clockwise by 60°)

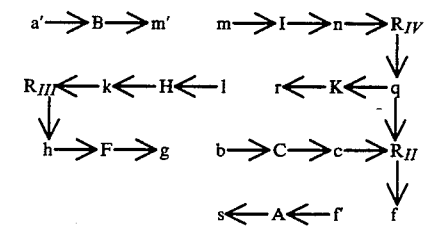

(Refer to FIG. 37(B))

(Reversely rotated position: liquid injection mode.
The rotor is rotated counterclockwise by 60°)

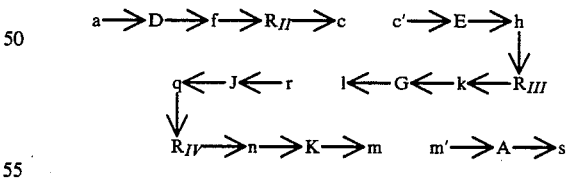

Figure 37C:
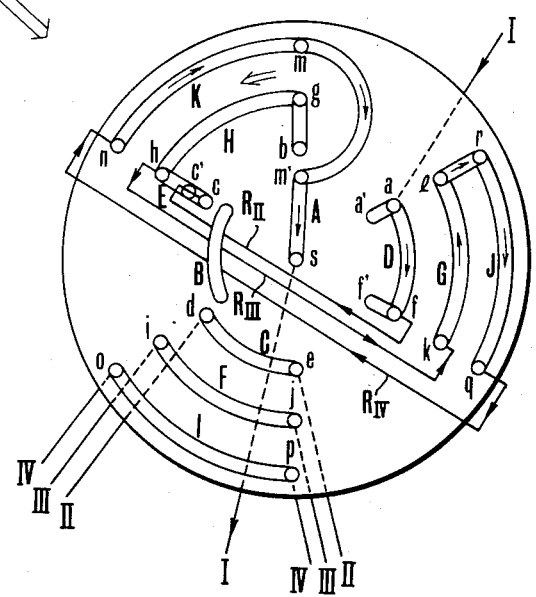

(Refer to FIG. 37(C))

Figure 36A:
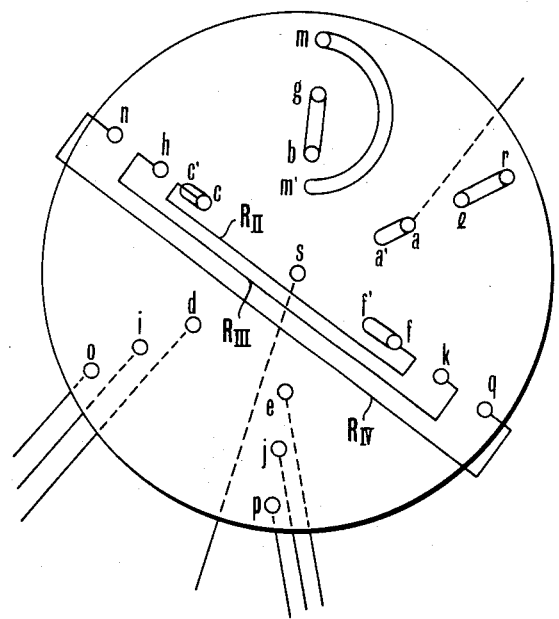
Figure 36B:
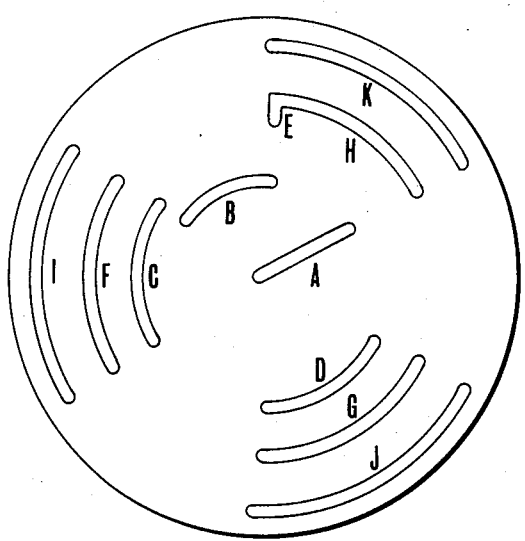

Therefore, the mode of injection of the liquid in the case of FIGS. 36(A) and 36(B) will be as shown in FIG. 37(D) in a normal rotation, and it will be as shown in FIG. 37(E) in a reverse rotation.

The present invention is not limited to those shown in the above described examples. A number of variations can be made within the scope of the invention. For example, if a positional change over between only FIG. 6(A) and FIG. 6(B) is made possible, and, further, a positional change over to FIG. 6(C) is made impossible by some suitable blocking means in a liquid injection device as shown in FIG. 3 through FIG. 6, such a device can be used as an ordinary liquid injection device, as has already been explained in reference to Example 1, in all other examples as well.

Also, since the grooves formed respectively on the stator and the rotor are actually a very fine line shape, and also since the rotor is usually made of polyimide, Teflon, etc. and is pressed against the stator in a mutually contacting manner with a sufficiently large amount of pressure, thus retaining a sufficient air-tightness or liquid-tightness, it is possible and easy to draw a variety of grooves geometrically as long as no difficulty arises in the flow of liquid. Therefore, the above-mentioned liquid injection device of a multi-function type for selectively injecting two kind of liquids can also have various shapes for the grooves as well as a variety of positionings for the small openings.

Further, a liquid injection device of the present invention is not only applied to the analysis of a sample solution in a flow injection analysis method and a liquid chromatography analysis method, etc., but can also be used advantageously as a device for mixing three or more kinds of liquids for applications other than analytical works (or a function of mixing two kinds of liquids, etc. may be additionally provided along with said function). For example, it can be used to supply a necessary reagent to a reaction system in which the reaction is made by a reagent being fed in liquid form. More specifically, the present invention may be utilized for the feeding of a reagent in liquid form to a reaction tank in the chemical industry in general or to a fermentation tank in microbiological fermentation.

Further, the column operation shown in FIGS. 17(A) through (E) for Example 6 can also be used in the other examples by providing a column or columns at a portion or all of the loops in an intervening manner, as a liquid injection device of similar column operation type.

As has been explained above, a liquid injection device according to the present invention has an advantage such that the selection of various functions for the injection of more than one kind of liquid in a variety of modes can be made by a simple operation. Such function can be achieved quite easily with a rotating operation of a rotor and a stator, and thus the structure is simple and an injection can be made precisely. Further, an additional advantage can be obtained such that the device can also be used as a passage change-over device or a column changeover device by replacing the loop parts with columns, etc. Thus the invention has a very large range of applications.

What is claimed is:

1. A liquid injection device, comprising a pair of a stator and a rotor arranged in such a manner so as to rotate in a mutually surface contacting relationship under an air-tight and light-tight states, a plurality of small openings for supplying liquid communicating to n number (wherein n is an integer of 3 or larger) of liquid systems, provided on the contacting surface of the rotor or stator and a plurality of bridging grooves for communicating two or more of said small openings to form a plurality of liquid flowing paths thereby, one of said plurality of bridging grooves being a main groove, provided on the contacting surface of said stator or rot whereby said rotor can be rotated to a predetermined angle in relation to the stator from its neutral position which forms a liquid filling mode to two other positions; that is a normally rotated position and a reversely rotated position, said liquid supply paths being formed at each one of the respective three positions following the conditions (a) and (b) shown below:

(a) a first liquid system out of said n number of liquid systems has a pair of small openings which serve as an inlet and an outlet for the supply of liquid, provided on one of the above-mentioned mutually contacting opposing surfaces, and said inlet and outlet are connected at the neutral position through the main groove, wherein said connection is shut off respectively at the above-mentioned normally rotated positions and reversely rotated positions; and (b) each one of the (n−1) number of other liquid systems other than the first liquid system has a loop which spans over two small openings connected to an external liquid supply channel, and there are also another two small openings, wherein at the neutral position each one of said loops is connected to its respective external liquid supply channel through the use of part of said plurality of bridging grooves, while at the the normally rotated and reversely rotated positions at leas a portion of the plurality of loops are connected to the inlet and the outlet of the first liquid system, each in a different manner.

2. A liquid injection device according to claim 1, wherein the loops are measuring tubes for filling liquid.

3. A liquid injection device according to claim 1, wherein at least a portion of said loops have a column or columns intervening therebetween.

4. A liquid injection device according to any one of claims 1 to 3, wherein two or more of the loops in the other liquid systems are connected in a series between the inlet and the outlet of the first liquid system at either the normally rotated position or the reversely rotated position.

5. A liquid injection device according to any one of claims 1 to 3, wherein two or more of the other liquid systems are connected in parallel between the inlet and the outlet of the first liquid system at either the normally rotated position or the reversely rotated position.

6. A liquid injection device according to any one of claims 1 to 3, wherein only a portion of the other liquid systems is connected between the inlet and the outlet of the first liquid system at one normally rotated position and one reversely rotated position, and the rest of the liquid systems of said other liquid systems excluding said portion of the liquid systems are connected between the inlet and the outlet of the first liquid system at another normally rotated position and another reversely rotated position.

7. A liquid injection device according to any one of claims 1 to 3, wherein the entire portion of the other liquid systems are connected in a series between the inlet and the outlet of the first liquid system, and the order of the other liquid systems will be reversed between the normally rotated position and the reversely rotated position.

8. A liquid injection device according to claim 7, wherein n is 3.

9. A liquid injection device according to any one of claims 1 to 3, wherein the small openings for supplying liquid are located on the circumference of the stator.

10. A liquid injection device according to claim 9, wherein n is 3.

11. A fluid injection device according to any one of claims 1 to 3, wherein either the small opening serving as the inlet or the small opening serving as the outlet of the first liquid system is at the central position of the stator.

12. A liquid injection device according to claim 11, wherein the first liquid is an eluant, the second liquid is a sample solution, and the third liquid is a reagent liquid.

* * * * *